US006849638B2

(12) United States Patent
Stolle et al.

(10) Patent No.: US 6,849,638 B2
(45) Date of Patent: Feb. 1, 2005

(54) 4-AMINO-5,6-SUBSTITUTED THIOPHENO [2, 3-D] PYRIMIDINES, PHARMACEUTICAL COMPOSITIONS CONTAINING THE SAME, AND THEIR USE IN THE TREATMENT OR PREVENTION OF PDE7$_B$-MEDIATED DISEASES AND CONDITIONS

(75) Inventors: Andreas Stolle, Wuppertal (DE); Donald E. Bierer, Bethany, CT (US); Yuanwei Chen, North Haven, CT (US); Dongping Fan, North Haven, CT (US); Barry Hart, Woodbridge, CT (US); Mary Katherine Monahan, Hamden, CT (US); William J. Scott, Guilford, CT (US)

(73) Assignee: Bayer Pharmaceuticals Corporation, West Haven, CT (US)

( * ) Notice: Subject to any disclaimer, the term of this patent is extended or adjusted under 35 U.S.C. 154(b) by 0 days.

(21) Appl. No.: 10/136,575

(22) Filed: Apr. 29, 2002

(65) Prior Publication Data

US 2003/0119829 A1 Jun. 26, 2003

Related U.S. Application Data

(60) Provisional application No. 60/287,629, filed on Apr. 30, 2001.

(51) Int. Cl.$^7$ .................... C07D 495/14; C07D 495/04; A61K 31/519; A61P 17/06; A61P 11/06
(52) U.S. Cl. ...................................... 514/267; 544/250
(58) Field of Search .......................... 544/250; 514/267

(56) References Cited

U.S. PATENT DOCUMENTS

| | | | |
|---|---|---|---|
| 3,627,766 A | | 12/1971 | Eichenberger et al. ... 260/256.5 R |
| 3,670,079 A | * | 6/1972 | Patanelli et al. ............. 514/172 |
| 3,681,351 A | | 8/1972 | Wellings .............. 260/256.5 R |
| 3,823,151 A | | 7/1974 | Eichenberger et al. .................... 260/294.8 C |
| 4,146,716 A | | 3/1979 | Cox et al. .................... 544/278 |
| 4,196,207 A | | 4/1980 | Webber ....................... 424/251 |
| 4,456,464 A | * | 6/1984 | Lee et al. .................... 504/195 |
| 4,526,608 A | * | 7/1985 | Lee ............................. 504/259 |
| 4,590,282 A | * | 5/1986 | Henrick ....................... 549/453 |
| 4,845,088 A | * | 7/1989 | Doherty et al. ............. 514/202 |
| 4,879,309 A | * | 11/1989 | Doll et al. .................. 514/513 |
| 4,933,339 A | * | 6/1990 | Sharma ................... 514/235.5 |
| 4,997,936 A | * | 3/1991 | Christensen et al. ........ 540/350 |
| 5,134,123 A | * | 7/1992 | Branca et al. ................ 514/18 |
| 5,356,903 A | * | 10/1994 | Eissenstat et al. .......... 514/311 |
| 6,316,439 B1 | * | 11/2001 | Kosley et al. ............. 514/215 |
| 6,423,716 B1 | | 7/2002 | Matsuno et al. ....... 514/252.02 |
| 6,506,762 B1 | * | 1/2003 | Horvath et al. .......... 514/259.4 |
| 6,552,192 B1 | * | 4/2003 | Hanus et al. ............... 544/280 |
| 2003/0187260 A1 | * | 10/2003 | Jonas et al. ................. 544/250 |
| 2004/0063943 A1 | * | 4/2004 | Eggenweiler et al. ....... 544/250 |

FOREIGN PATENT DOCUMENTS

| | | | | |
|---|---|---|---|---|
| EP | 0 452 002 | | 10/1991 | |
| JP | 01313480 A | * | 12/1989 | ....... C07D/491/147 |
| WO | WO 99/46267 | | 9/1999 | |
| WO | WO 00/59912 | | 10/2000 | |

OTHER PUBLICATIONS

Ghorab, Phosphorous, Sulfur and Silicon and the Related Elements, 165, 221–235 (2000).*

Sabnis et al., "Synthesis of thieno[2,3–d]pyrimidine derivatives and their fluorescent and biological properties", *Indian J. Tech.*, 28(2), pp. 54–58 (1990).

Po tacek et al., "Reactions of 2–Ethoxymethyleneamino–3–cyano–4,5,6,7–tetrahydrobenzo[b]thiophene with Nitrogen Nucleophiles", *Chem. Pap.*, 46(1), pp. 34–37 (1992).

Dave et al., "Gould–Jacob type of reaction in the synthesis of thieno[3,2–e]pyrimido[1,2–c]pyrimidines: a comparison of classical heating vs. solvent–free microwave irradiation", *Heterocycles*, 51(8), pp. 1819–1826 (1999).

Patil et al., "Synthesis of7–methyl–4–substituted–5,6,7, 8–tetrahydrobenzo[b]thieno [2,3,–d]pyrimidines as antimicrobial agents", *J. Indian Chem. Soc.*, 68(3), pp. 169–171 (1991).

Ram, "Organosulfur Compounds as Potential Pesticides", *Arch. Pharm.* (Weinheim, Ger.), 313(5), pp. 471–476 (1980).

Ram, "Thieno [2,3–d]pyrimidines as Potential Chemotherapeutic Agents". *Arch Pharm.* (Weinheim, Ger.), 312(1), pp. 19–25 (1979).

Jordis et al., "7,9–Dideaza–9–thiaadenines(4–aminothieno [2,3–d]pyrimidines) as potential anticytokinines)", *Vestn.Slov.Kem.Drus.*, 33(3), pp. 217–238 (1986).

Ram et al., "Thieno[2,3–d]pyrimidines as Potential Chemotherapeutic Agents. II.", *J. Heterocycl.Chem.*, 18(7), pp. 1277–1280 (1981).

Moneer et al., "Synthesis of certain thienopyrimidines of anticipated analgesic activity" *Egypt J. Pharm. Sci.*, 34(4–6) 623–641 (1993).

Moneer et al., "Reaction of 3–Amino–and 4 hydrazion 5,6 tetramenthylenethienzo [2,3–d] pyrimidine derivatives with azlactones", *Egypt J. Pharm. Sci.*, 34(4–6), pp. 599–609 (1993).

(List continued on next page.)

*Primary Examiner*—Mark L. Berch
(74) *Attorney, Agent, or Firm*—Connolly Bove Lodge & Hutz LLP

(57) ABSTRACT

The invention relates to 4-amino-5,6-substituted thiopheno [2,3-d] pyrimidines, pharmaceutical compositions containing the same and their use to treat or prevent diseases and conditions mediated by the phosphodiesterase enzyme 7$_B$ (PDE7$_B$). Diseases and conditions mediated by PDE7$_B$ include osteoporosis, osteopenia and asthma.

12 Claims, No Drawings

OTHER PUBLICATIONS

Arya, "Synthesis of new heterocycles: Part VI.—Synthesis of certain novel condensed thiophenes", *Ind. J. Chem.,* 10(12), pp. 1141–1150 (1972).

Robba et al., "Synthesis of 5,6,7,8–tetrahydrobeno[1]thieno [2,3,d]pyrimidines", *C. R. Acad. Sci. Paris,* t.276, pp. 93–95 (1973).

Darias et al., "Antihistaminic thienopyrimidine derivatives", *Chim. Ther.,* 7(3), pp. 224–227 (1972).

Devani et al., "Synthesis of 2–aminothiophenes & thieno[2, 3–d]pyrimidines", *Indian J. Chem.,* 14B, pp. 357–360 (May 1976).

Taylor et al. "Heterocyclic synthesis from aminonitriles. XXIX. A new synthesis of 5–substituted pyrimidines", *J. Org. Chem.,* 32(8), pp. 2376–2378 (1967).

Foye et al., "Antiradiation Compounds XIV: Dithiocarbamates of Aminothiophenes", *J. Pharm. Sci.,* 59(9), pp. 1348–1350 (1970).

Miyashita et al., "Aroylation of fused pyrimidines; synthesis of 4–aroylfuro[2,3–d], 4–aroylthieno[2,3–d], and 4–aroylisoxazolo[5,4–d]pyrimidines", *Heterocycles,* 45(11), pp. 2159–2173 (1997).

Abstract of DD272066 (Sep. 27, 1989).

Ismail et al., "Synthesis and antimicrobial activity of some tetramethylene–ethieno[2,3–d] pyrimidine derivatives", *Farmaco,* 50(9), pp. 611–616 (1995).

Jordis et al., "7,9–Dideaza–9–thiaadenines (4–aminothieno [2,3–d]pyrimidines) as potential anticytokinins", *Vestn.Slov. Kem. Drus.,* 33(3), pp. 217–238 (1986).

Gardner et al., Cloning and Characterization of the Human and Mouse PDE7B, a Novel cAMP–Specific Cyclic Nucleotide Phosphodiesterase. *Biochemical and Biophysical Research Communications,* 272, 186–192 (2000).

Sasaki et al., Novel alternative splice variants of rat phosphodiesterase 7B showing unique tissue–specific expression and phosphorylation. *Biochem J.* (2002), 361, 211–220.

* cited by examiner

4-AMINO-5,6-SUBSTITUTED THIOPHENO [2, 3-D] PYRIMIDINES, PHARMACEUTICAL COMPOSITIONS CONTAINING THE SAME, AND THEIR USE IN THE TREATMENT OR PREVENTION OF $PDE7_B$-MEDIATED DISEASES AND CONDITIONS

CROSS-REFERENCE TO RELATED APPLICATIONS

This application is a continuation-in-part of U.S. Application Ser. No. 60/287,629, filed Apr. 30, 2001, which is hereby incorporated herein in its entirety.

FIELD OF THE INVENTION

The invention relates to 4-amino-5,6-substituted thiopheno [2,3-d] pyrimidines, pharmaceutical compositions containing the same and their use to treat or prevent diseases and conditions mediated by the phosphodiesterase enzyme $7_B$ ($PDE7_B$). Diseases and conditions mediated by $PDE7_B$ include osteoporosis, osteopenia and asthma. The invention also relates to processes for preparing 4-amino-5, 6-substituted thiopheno[2,3-d] pyrimidines and processes for preparing compositions containing the same.

BACKGROUND

Cyclic nucleotide phosphodiesterases (PDEs) show specificity for purine cyclic nucleotide substrates and catalyze cyclic AMP (cAMP) and cyclic GMP (cGMP) hydrolysis (Thompson, W. J. (1991) *Pharma. Ther.* 51:13–33). Cyclic nucleotide phosphodiesterases regulate the steady-state levels of cAMP and cGMP and modulate both the amplitude and duration of cyclic nucleotide signal. These cyclic nucleotides are important second messengers in many physiological processes, including regulation of vascular resistance, cardiac output, visceral motility, immune response, inflammation, neuroplasticity, vision, and reproduction (Hetman, J. M. (2000) *Proc. Nat. Acad. Sci.* 97: 472–476). At least ten different but homologous PDE gene families are currently known to exist in mammalian tissues (Sasaki, T. et al. (2000) *Biochem. Biophys. Res. Comm.* 271(3):575–583). Most families contain distinct genes, many of which are expressed in different tissues as functionally unique alternative splice variants. (Beavo (1995) *Physiological Reviews* 75:725–748 and U.S. Pat. No. 5,798,246).

All cyclic nucleotide phosphodiesterases contain a core of about 270 conserved amino acids in the COOH-terminal half of the protein thought to be the catalytic domain of the enzyme. A conserved motif of the sequence HDXXHXX has been identified in the catalytic domain of all cyclic nucleotide phosphodiesterases isolated to date. The cyclic nucleotide phosphodiesterases within each family display about 65% amino acid homology and the similarity drops to less than 40% when compared between different families with most of the similarity occurring in the catalytic domains.

Most cyclic nucleotide phosphodiesterase genes have more than one alternatively spliced mRNA transcribed from them and in many cases the alternative splicing appears to be highly tissue specific, providing a mechanism for selective expression of different cyclic nucleotide phosphodiesterases (Beavo supra). Cell-type-specific expression suggests that the different isozymes are likely to have different cell-type-specific properties.

Type 1 cyclic nucleotide phosphodiesterases are $Ca^{2+}$/calmodulin dependent, are reported to contain three different genes, each of which appears to have at least two different splice variants, and have been found in the lung, heart and brain. Some of the calmodulin-dependent phosphodiesterases are regulated in vitro by phosphorylation/dephosphorylation events. The effect of phosphorylation is to decrease the affinity of the enzyme for calmodulin, which decreases phosphodiesterase activity, thereby increasing the steady state level of cAMP. Type 2 cyclic nucleotide phosphodiesterases are cGMP stimulated, are localized in the brain and are thought to mediate the effects of cAMP on catecholamine secretion. Type 3 cyclic nucleotide phosphodiesterases are cGMP-inhibited, have a high specificity for cAMP as a substrate, and are one of the major phosphodiesterase isozymes present in vascular smooth muscle and play a role in cardiac function. One isozyme of type 3 is regulated by one or more insulin-dependent kinases.

Type 4 cyclic nucleotide phosphodiesterases are the predominant isoenzyme in most inflammatory cells, with some of the members being activated by cAMP-dependent phosphorylation. Type 5 cyclic nucleotide phosphodiesterases have traditionally been thought of as regulators of cGMP function but may also affect cAMP function. High levels of type 5 cyclic nucleotide phosphodiesterases are found in most smooth muscle preparations, platelets and kidney. Type 6 cyclic nucleotide phosphodiesterase family members play a role in vision and are regulated by light and cGMP.

$PDE7_{A2}$, a Type 7 cyclic nucleotide phosphodiesterase family member, is found in high concentrations in skeletal muscle. Work using mouse tissue has shown that $PDE7_{A2}$ is found in high concentrations in skeletal muscle, followed by spleen. Lower levels were found in brain, heart, kidney, lung, and uterus (Han, P. et al. (1997) *J. Biol. Chem.* 272:16152–16157). A member of the type 7 cyclic nucleotide phosphodiesterases identified as $PDE7_B$ has been cloned (Hetman, supra). In the mouse, $PDE7_B$ has been found in high concentrations in pancreas followed by brain, heart, skeletal muscle, eye, thyroid, ovary, testis, submaxillary gland, epididymus, and liver. $PDE7_B$ has been identified as a cAMP-specific PDE (Hetman, supra). A human $PDE7_B$ cDNA was cloned by Sasaki et al. and a dot blot analysis was made to determine the expression pattern of $PDE7_B$ in human tissues. Human $PDE7_B$ transcripts were particularly abundant in the putamen and caudate nucleus. Sasaki et al. reported the effects of various PDE inhibitors on recombinant human $PDE7_B$. The human $PDE7_B$ gene is thought to be localized at chromosome 6q23–24. The EPM2A gene, which is related to progressive myoclonus epilepsy, is located at 6q24, making it possible that $PDE7_B$ and its gene is linked to epilepsy (Sasaki et al., supra). Gardner et al. ((2000) *Biochem. Biophys. Res. Comm.* 272:186–192) also identified and characterized human $PDE7_B$. Gardner et al. reported that mRNA for human $PDE7_B$ was most highly expressed in caudate nucleus, putamen, and occipital lobe of the brain, heart, liver, ovary, pituitary gland, kidney, small intestine, and thymus. A phylogenetic alignment of the 230 amino acid catalytic domain of $PDE7_B$ (amino acids 172–420) with representatives of other PDEs showed that $PDE7_B$ has the highest homology to and clusters with PDE7A (70% identity). Gardner et al. also studied the effects of a variety of standard PDE inhibitors on $PDE7_B$.

A listing of cyclic nucleotide phosphodiesterase families 1–7, their localization and physiological role is given in Beavo supra. A Type 8 family is reported in U.S. Pat. No. 5,798,246.

Many functions of the immune and inflammatory responses are inhibited by agents that increase intracellular levels of cAMP (Verghese (1995) *Mol. Pharmacol.* 47:1164–1171) while the metabolism of cGMP is involved in smooth muscle, lung and brain cell function (Thompson W. (1991) *Pharma. Ther.* 51:13–33). A variety of diseases have been attributed to increased cyclic nucleotide phosphodiesterase activity which results in decreased levels of cyclic nucleotides. For example, one form of diabetes insipidus in the mouse has been associated with increased phosphodiesterase Family 4 activity and an increase in low-$K_m$ cAMP phosphodiesterase activity has been reported in leukocytes of atopic patients. Defects in cyclic nucleotide phosphodiesterases have also been associated with retinal disease. Retinal degeneration in the rd mouse, human autosomal recessive retinitis pigmentosa, and rod/cone dysplasia 1 in Irish setter dogs have been attributed to mutations in the Family 6 phosphodiesterase, gene B. Family 3 phosphodiesterase has been associated with cardiac disease.

Many inhibitors of different cyclic nucleotide phosphodiesterases have been identified and some have undergone clinical evaluation. For example, Family 3 phosphodiesterase inhibitors are being developed as antithrombotic agents, as antihypertensive agents and as cardiotonic agents useful in the treatment of congestive heart failure. Rolipram, a Family 4 phosphodiesterase inhibitor, has been used in the treatment of depression and other inhibitors of Family 4 phosphodiesterase are undergoing evaluation as anti-inflammatory agents. Rolipram has also been shown to inhibit lipopolysaccharide (LPS) induced TNF-alpha which has been shown to enhance HIV-1 replication in vitro. Therefore, rolipram may inhibit HIV-1 replication (Angel et al. (1995) *AIDS* 9:1137–44). Additionally, based on its ability to suppress the production of TNF alpha and beta and interferon gamma, rolipram has been shown to be effective in the treatment of encephalomyelitis, the experimental animal model for multiple sclerosis (Sommer et al. (1995) *Nat. Med.* 1:244–248) and may be effective in the treatment of tardive dyskinesia (Sasaki et al. (1995) *Eur. J. Pharmacol.* 282:72–76).

There are also nonspecific phosphodiesterase inhibitors such as theophylline, used in the treatment of bronchial asthma and other respiratory diseases, and pentoxifylline, used in the treatment of intermittent claudication and diabetes-induced peripheral vascular disease. Theophylline is thought to act on airway smooth muscle function as well as in an anti-inflammatory or immunomodulatory capacity in the treatment of respiratory diseases (Banner et al. (1995) *Eur. Respir. J* 8:996–1000) where it is thought to act by inhibiting both cyclic nucleotide phosphodiesterase cAMP and cGMP hydrolysis (Banner et al. (1995) *Monaldi Arch. Chest Dis.* 50:286–292). Pentoxifylline, also known to block TNF-alpha production, may inhibit HIV-1 replication (Angel et al. supra). Thiopyrimidine derivatives substituted at position 2 of the pyrimidine ring have been taught as inhibitors of cGMP or thromboxane $A_2$ ($TXA_2$), which is known to induce platelet aggregation and to contract smooth muscle (U.S. Pat. No. 5,869,486). A list of cyclic nucleotide phosphodiesterase inhibitors is given in Beavo supra.

Cyclic nucleotide phosphodiesterases have also been reported to affect cellular proliferation of a variety of cell types and have been implicated in the treatment of various cancers. Bang et al. ((1994) *Proc. Natl. Acad. Sci. USA* 91:5330–5334) reported that the prostate carcinoma cell lines DU 145 and LNCaP were growth-inhibited by delivery of cAMP derivatives and phosphodiesterase inhibitors and observed a permanent conversion in phenotype from epithelial to neuronal morphology; Matousovic et al. ((1995) *J. Clin. Invest.* 96:401–410) suggest that cyclic nucleotide phosphodiesterase isozyme inhibitors have the potential to regulate mesangial cell proliferation; Joulain et al. ((1995) *J. Mediat. Cell Signal* 11:63–79) reports that cyclic nucleotide phosphodiesterase has been shown to be an important target involved in the control of lymphocyte proliferation; and Deonarain et al. ((1994) *Brit. J. Cancer* 70:786–94) suggest a tumor targeting approach to cancer treatment that involves intracellular delivery of phosphodiesterases to particular cellular compartments, resulting in cell death.

Accordingly, compounds that interact with cyclic nucleotide phosphodiesterases may provide treatments for various diseases and conditions caused by errors in regulation of cyclic nucleotide phosphodiesterase mediated processes. The present invention advances the state of the art by providing such compounds.

SUMMARY OF THE INVENTION

The invention provides compounds that inhibit the activity of $PDE7_B$, particularly 4-amino-5,6-substituted thiopheno [2,3-d] pyrimidines. The invention further provides pharmaceutical compositions containing such compounds and processes for preparing such compounds and compositions. Finally, the invention provides for methods of treating a mammal for diseases or conditions caused by $PDE7_B$-mediated processes by administering to the mammal an effective amount of a compound that inhibits the activity of $PDE7_B$, particularly 4-amino-5,6-substituted thiopheno [2,3-d] pyrimidines.

The invention relates to compounds of the formulas I–IV.

The invention includes a compound according to formula I:

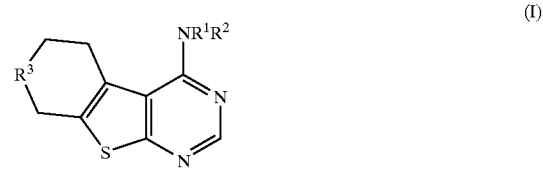

(I)

wherein
R$^1$ and R$^2$ are independently selected from the group consisting of
hydrogen,
alkyl of 1–8 carbon atoms,
alkenyl of 2–8 carbon atoms,
alkynyl of 2–8 carbon atoms,
cycloalkyl of 3–7 carbon atoms,
heterocycloalkyl of 2–6 carbon atoms and 1–2 heteroatoms selected from NH, S and O,
aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O,
heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O, and $R^4$–$R^5$, or $R^1$ and $R^2$ combine to form, together with the nitrogen atom to which they are attached, a 5–7 membered saturated ring which may contain 1–2 additional heteroatoms selected from the group consisting of NH, $NR^8$, S and O, or combine to form, together with the nitrogen atom to which they are attached, a 5–7 membered unsaturated ring which may contain 1–2 additional heteroatoms selected from the group consisting of N, S and O, wherein said saturated or unsaturated ring may be substituted with 1–2 substituents selected from the group consisting of OH, alkyl of 1–6 carbon atoms, alkenyl of 2–6 carbon atoms, alkynyl of 2–6 carbon atoms, cycloalkyl of 3–7 carbon atoms, heterocylcoalkyl of 2–6 carbon atoms and 1–2 heteroatoms selected from NH, S and O, halogen, haloalkyl of 1–2 carbon atoms and a number of halogen atoms up to the perhalo level, alkoxy of 1–6 carbon atoms, haloalkoxy of 1–6 carbon atoms and a number of halogen atoms up to the perhalo level, and $R^9$–$R^{10}$;

$R^3$ is selected from the group consisting of NH, $NR^{11}$, S, $S(=O)_2$, and O; with the proviso that $R^3$ is not NH when both $R^1$ and $R^2$ are methyl; with the further proviso that $R^1$ is not butyl, phenyl, or benzyl when $R^2$ is hydrogen and $R^3$ is S or O;

$R^4$ is selected from
alkyl of 1–8 carbon atoms,
alkenyl of 2–8 carbon atoms,
alkynyl 2–8 carbon atoms,
$C(=O)$,
$S(=O)_2$, and
$C(=O)O$—;

$R^5$ is selected from
hydrogen,
OH,
alkyl of 1–8 carbon atoms,
alkenyl 2–8 carbon atoms,
alkynl 2–8 carbon atoms,
alkoxy of 1–8 carbon atoms,
thioxy of 1–8 carbon atoms,
aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms and heteroaryl of 4–11 carbon atoms and 1–2 heteroatoms selected from N, S and O,
heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms and heteroaryl of 4–11 carbon atoms and 1–2 heteroatoms selected from N, S and O,
cycloalkyl of 3–7 carbon atoms,
heterocycloalkyl of 2–6 carbon atoms and 1–2 heteroatoms selected from NH, S and O, and
N—$R^6$–$R^7$,
with the proviso that $R^5$ is not OH, thioxy, alkoxy or N—$R^6$–$R^7$ when $R^4$ is $C(=O)O$—, and with the further proviso that $R^5$ is not alkyl when $R^4$ is alkyl, alkenyl or alkynyl;

$R^6$ and $R^7$ are independently selected from
hydrogen,
alkyl of 1–8 carbon atoms,
alkenyl of 2–8 carbon atoms, and
alkynyl of 2–8 carbon atoms, or $R^6$ and R combine together with the nitrogen atom to which they are attached to form a 5–7 membered, unsaturated ring which may contain 1–2 additional heteroatoms selected from N, S and O or to form a 5–7 membered, saturated ring which may contain 1–2 additional heteroatoms selected from NH, $NR^{11}$, S and O;

$R^8$ is selected from
alkyl of 1–8 carbon atoms,
alkenyl of 2–8 carbon atoms,
alkynyl of 2–8 carbon atoms,
$R^{12}$–$R^{13}$,
cycloalkyl of 3–7 carbon atoms,
heterocycloalkyl of 2–6 carbon atoms and 1–2 heteroatoms selected from NH, S and O,
aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O,
heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O;

$R^9$ is selected from
alkyl of 1–8 carbon atoms,
alkenyl of 2–8 carbon atoms, and
alkynyl of 2–8 carbon atoms;

$R^{10}$ is selected from
OH,
aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O, and
heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O;

$R^{11}$ is benzyl which may be substituted with alkyl of 1–6 carbon atoms, alkenyl of 2–6 carbon atoms, alkynyl of 2–6 carbon atoms, halogen, and $R^{14}$–$R^{15}$;

with the proviso that when $R^{11}$ is benzyl substituted with methyl or halogen, then $R^1$ and $R^2$ are not both methyl or if $R^1$ is hydrogen, then $R^2$ is not alkenyl of 3 carbon atoms or methyl, with the further proviso that when $R^{11}$ is benzyl substituted with t-butyl alkyl, and $R^1$ is hydrogen or methyl, then $R^2$ is not methyl;

$R^{12}$ is selected from
alkyl of 1–8 carbon atoms,
alkenyl of 2–8 carbon atoms, and
alkynyl of 2–8 carbon atoms;

$R^{13}$ is selected from
cycloalkyl of 3–7 carbon atoms,
heterocycloalkyl of 2–6 carbon atoms and 1–2 heteroatoms selected from NH, S and O,
aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O, and
heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O;
or $R^1$ and $R^2$ combine to form, together with the nitrogen atom to which they are attached, a 5–7 membered saturated ring or a 8–10 membered bicyclic saturated ring;

$R^{14}$ is alkyl of 1–3 carbon atoms;
$R^{15}$ is cylcoalkyl of 3–7 carbon atoms;
and pharmaceutically acceptable salts thereof.

The invention also includes a compound according to formula II:

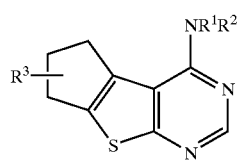

(II)

wherein
$R^1$ and $R^2$ are independently selected from the group consisting of
hydrogen,
alkyl of 1–8 carbon atoms,
alkenyl of 2–8 carbon atoms,
alkynyl of 2–8 carbon atoms,
cycloalkyl of 3–7 carbon atoms,
heterocycloalkyl of 2–6 carbon atoms and 1–2 heteroatoms selected from NH, S and O,
aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O,
heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O, and
$R^4$–$R^5$,
or $R^1$ and $R^2$ combine to form, together with the nitrogen atom to which they are attached, a 5–7 membered saturated ring which may contain 1–2 additional heteroatoms selected from the group consisting of NH, $NR^8$, S and O, or combine to form, together with the nitrogen atom to which they are attached, a 5–7 membered unsaturated ring which may contain 1–2 additional heteroatoms selected from the group consisting of N, S and O,
wherein said saturated or unsaturated ring may be substituted with 1–2 substituents selected from the group consisting of OH, alkyl of 1–6 carbon atoms, alkenyl of 2–6 carbon atoms, alkynyl of 2–6 carbon atoms, cycloalkyl of 3–7 carbon atoms, heterocyloalkyl of 2–6 carbon atoms and 1–2 heteroatoms selected from NH, S and O, halogen, haloalkyl of 1–2 carbon atoms and a number of halogen atoms up to the perhalo level, alkoxy of 1–6 carbon atoms, haloalkoxy of 1–6 carbon atoms and a number of halogen atoms up to the perhalo level, and $R^9$–$R^{10}$;

$R^3$ is selected from the group consisting of:
hydrogen,
alkyl of 1–8 carbon atoms,
alkenyl of 2–8 carbon atoms,
alkynyl of 2–8 carbon atoms,
cycloalkyl of 3–7 carbon atoms,
heterocycloalkyl of 2–6 carbon atoms and 1–2 heteroatoms selected from NH, S and O,
aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O, heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O, and $R^4$–$R^5$;

$R^4$ is selected from
alkyl of 1–8 carbon atoms,
alkenyl of 2–8 carbon atoms,
alkynyl 2–8 carbon atoms,
C(=O),
S(=O)$_2$, and
C(=O)O—;

$R^5$ is selected from
hydrogen,
OH,
alkyl of 1–8 carbon atoms,
alkenyl 2–8 carbon atoms,
alkynyl 2–8 carbon atoms,
alkoxy of 1–8 carbon atoms,
thioxy of 1–8 carbon atoms,
aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms and heteroaryl of 4–11 carbon atoms and 1–2 heteroatoms selected from N, S and O, heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms and heteroaryl of 4–11 carbon atoms and 1–2 heteroatoms selected from N, S and O, cycloalkyl of 3–7 carbon atoms,
heterocycloalkyl of 2–6 carbon atoms and 1–2 heteroatoms selected from
NH, S and O, and
N—$R^6$–$R^7$,
with the proviso that $R^5$ is not OH, thioxy, alkoxy or N—$R^6$–$R^7$ when $R^4$ is C(=O)O—, and with the further proviso that $R^5$ is not alkyl when $R^4$ is alkyl, alkenyl or alkynyl;

$R^6$ and $R^7$ are independently selected from
hydrogen,
alkyl of 1–8 carbon atoms,
alkenyl of 2–8 carbon atoms, and
alkynyl of 2–8 carbon atoms,
or $R^6$ and $R^7$ combine together with the nitrogen atom to which they are attached to form a 5–7 membered, unsaturated ring which may contain 1–2 additional heteroatoms selected from N, S and O or to form a 5–7 membered, saturated ring which may contain 1–2 additional heteroatoms selected from NH, NR$^{11}$, S and O;

$R^8$ is selected from
alkyl of 1–8 carbon atoms,
alkenyl of 2–8 carbon atoms,
alkynyl of 2–8 carbon atoms,
$R^{12}$–$R^{13}$,
cycloalkyl of 3–7 carbon atoms,
heterocycloalkyl of 2–6 carbon atoms and 1–2 heteroatoms selected from NH, S and O,
aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O, heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O;

$R^9$ is selected from
alkyl of 1–8 carbon atoms,
alkenyl of 2–8 carbon atoms, and
alkynyl of 2–8 carbon atoms;

$R^{10}$ is selected from
OH,
aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O, and heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O;

$R^{11}$ is benzyl which may be substituted with
alkyl of 1–6 carbon atoms,
alkenyl of 2–6 carbon atoms,
alkynyl of 2–6 carbon atoms,
halogen, and
$R^{14}$–$R^{15}$;

$R^{12}$ is selected from
  alkyl of 1–8 carbon atoms,
  alkenyl of 2–8 carbon atoms, and
  alkynyl of 2–8 carbon atoms;
$R^{13}$ is selected from
  cycloalkyl of 3–7 carbon atoms,
  heterocycloalkyl of 2–6 carbon atoms and 1–2 heteroatoms selected from NH, S and O,
  aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O, and
  heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O;
$R^{14}$ is alkyl of 1–3 carbon atoms;
$R^{15}$ is cylcoalkyl of 3–7 carbon atoms;
with the proviso that when $R^3$ is hydrogen,
$R^1$ and $R^2$ are independently selected from the group consisting of
  hydrogen, with the further proviso that $R^1$ and $R^2$ are not both hydrogen, alkyl of 1–8 carbon atoms, with the further proviso that $R^1$ and $R^2$ are not both ethyl,
  alkenyl of 2–8 carbon atoms,
  alkynyl of 2–8 carbon atoms,
  heterocycloalkyl of 4–6 carbon atoms and 1–2 heteroatoms selected from NH, S and O, and
  bornyl,
or $R^1$ and $R^2$ combine to form, together with the nitrogen atom to which they are attached,
  a 5–7 membered saturated ring which contains 1–2 sulfur atoms, or
  an 8–10 membered bicyclic saturated ring;
and pharmaceutically acceptable salts thereof.

The invention also includes a compound according to formula III:

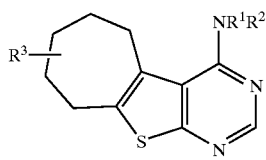

(III)

wherein
$R^1$ and $R^2$ are independently selected from the group consisting of
  hydrogen,
  alkyl of 1–8 carbon atoms,
  alkenyl of 2–8 carbon atoms,
  alkynyl of 2–8 carbon atoms,
  alkoxy of 1–8 carbon atoms,
  cycloalkyl of 3–7 carbon atoms,
  heterocycloalkyl of 2–6 carbon atoms and 1–2 heteroatoms selected from NH, S and O,
  aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O,
  heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O, and
  $R^4$–$R^5$,
or $R^1$ and $R^2$ combine to form, together with the nitrogen atom to which they are attached, a 5–7 membered saturated ring which may contain 1–2 additional heteroatoms selected from the group consisting of NH, $NR^8$, S and O, or combine to form, together with the nitrogen atom to which they are attached, a 5–7 membered unsaturated ring which may contain 1–2 additional heteroatoms selected from the group consisting of N, S and O,
  wherein said saturated or unsaturated ring may be substituted with 1–2 substituents selected from the group consisting of OH, alkyl of 1–6 carbon atoms, alkenyl of 2–6 carbon atoms, alkynyl of 2–6 carbon atoms, cycloalkyl of 3–7 carbon atoms, heterocyloalkyl of 2–6 carbon atoms and 1–2 heteroatoms selected from NH, S and O, halogen, haloalkyl of 1–2 carbon atoms and a number of halogen atoms up to the perhalo level, alkoxy of 1–6 carbon atoms, haloalkoxy of 1–6 carbon atoms and a number of halogen atoms up to the perhalo level, and $R^9$–$R^{10}$;
$R^3$ is selected from the group consisting of:
  hydrogen,
  alkyl of 1–8 carbon atoms,
  alkenyl of 2–8 carbon atoms,
  alkynyl of 2–8 carbon atoms,
  cycloalkyl of 3–7 carbon atoms,
  heterocycloalkyl of 2–6 carbon atoms and 1–2 heteroatoms selected from NH, S and O,
  aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O,
  heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O, and $R^4$–$R^5$, $R^4$ is selected from
alkyl of 1–8 carbon atoms,
alkenyl of 2–8 carbon atoms,
alkynyl 2–8 carbon atoms,
C(=O),
S(=O)$_2$, and
C(=O)O—;

$R^5$ is selected from
hydrogen,
OH,
alkyl of 1–8 carbon atoms,
alkenyl 2–8 carbon atoms,
alkynyl 2–8 carbon atoms,
alkoxy of 1–8 carbon atoms,
thioxy of 1–8 carbon atoms,
aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms and heteroaryl of 4–11 carbon atoms and 1–2 heteroatoms selected from N, S and O,
heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms and heteroaryl of 4–11 carbon atoms and 1–2 heteroatoms selected from N, S and O,
cycloalkyl of 3–7 carbon atoms,
heterocycloalkyl of 2–6 carbon atoms and 1–2 heteroatoms selected from NH, S and O, and
N—$R^6$-$R^7$,
with the proviso that $R^5$ is not OH, thioxy, alkoxy or N—$R^6$-$R^7$ when $R^4$ is C(=O)O—, and with the further proviso that $R^5$ is not alkyl when $R^4$ is alkyl, alkenyl or alkynyl;

$R^6$ and $R^7$ are independently selected from
hydrogen,
alkyl of 1–8 carbon atoms,
alkenyl of 2–8 carbon atoms, and
alkynyl of 2–8 carbon atoms,
or $R^6$ and $R^7$ combine together with the nitrogen atom to which they are attached to form a 5–7 membered, unsaturated ring which may contain 1–2 additional heteroatoms selected from N, S and O or to form a 5–7 membered, saturated ring which may contain 1–2 additional heteroatoms selected from NH, NR$^{11}$, S and O;

$R^8$ is selected from
alkyl of 1–8 carbon atoms,
alkenyl of 2–8 carbon atoms,
alkynyl of 2–8 carbon atoms,
$R^{12}$–$R^{13}$,
cycloalkyl of 3–7 carbon atoms,
heterocycloalkyl of 2–6 carbon atoms and 1–2 heteroatoms selected from NH, S and O,
aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O,
heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O;

$R^9$ is selected from
alkyl of 1–8 carbon atoms,
alkenyl of 2–8 carbon atoms, and
alkynyl of 2–8 carbon atoms;

$R^{10}$ is selected from
OH,
aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O, and
heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O;

$R^{11}$ is benzyl which may be substituted with
alkyl of 1–6 carbon atoms,
alkenyl of 2–6 carbon atoms,
alkynyl of 2–6 carbon atoms,
halogen, and
$R^{14}$–$R^{15}$;

$R^{12}$ is selected from
alkyl of 1–8 carbon atoms,
alkenyl of 2–8 carbon atoms, and
alkynyl of 2–8 carbon atoms;

R¹³ is selected from
  cycloalkyl of 3–7 carbon atoms,
  heterocycloalkyl of 2–6 carbon atoms and 1–2 heteroatoms selected from NH, S and O,
  aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O, and
  heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O;

$R^{14}$ is alkyl of 1–3 carbon atoms;
$R^{15}$ is cylcoalkyl of 3–7 carbon atoms;
with the proviso that when $R^3$ is hydrogen,
$R^1$ and $R^2$ are independently selected from the group consisting of
  hydrogen, with the further proviso that only one of $R^1$ and $R^2$ may be hydrogen,
  alkyl of 1–8 carbon atoms,
  alkenyl of 2–8 carbon atoms,
  alkynl of 2–8 carbon atoms,
  alkoxy of 1–8 carbon atoms,
  cycloalkyl of 3–7 carbon atoms,
  phenyl which may be substituted from one to five times with bromine,
  chlorine, $CH_3$, or $CF_3$, and
  $R^4$–$R^5$, with the further proviso that if $R^4$ is methyl then R may not be a five membered ring that contains oxygen as one member of the ring and that if $R^4$ is ethyl then $R^5$ may not be substituted or unsubstituted phenyl,
or
$R^1$ and $R^2$ combine to form, together with the nitrogen atom to which they are attached, a 6–7 membered saturated ring which may contain 1–2 additional heteroatoms selected from the group consisting of NH, $NR^8$, S, and O, or combine to form, together with the nitrogen atom to which they are attached, a 6–7 membered unsaturated ring which may contain 1–2 additional heteroatoms selected from the group consisting of N, S and O,
  wherein said saturated or unsaturated ring may be substituted with 1–2 substituents selected from the group consisting of OH, alkyl of 1–6 carbon atoms, alkenyl of 2–6 carbon atoms, alkynyl of 2–6 carbon atoms, cycloalkyl of 3–7 carbon atoms, heterocycloalkyl of 2–6 carbon atoms and 1–2 heteroatoms selected from NH, S and O, halogen, haloalkyl of 1–2 carbon atoms and a number of halogen atoms up to the perhalo level, alkoxy of 1–6 carbon atoms, haloalkoxy of 1–6 carbon atoms and a number of halogen atoms up to the perhalo level, and $R^9$–$R^{10}$;
and pharmaceutically acceptable salts thereof.

The invention also includes a compound according to the formula IV:

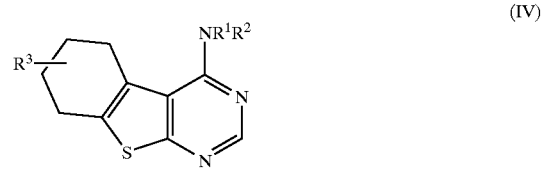

(IV)

wherein
$R^1$ and $R^2$ are independently selected from the group consisting of
  hydrogen,
  alkyl of 1–8 carbon atoms,
  alkenyl of 2–8 carbon atoms,
  alkynyl of 2–8 carbon atoms,
  cycloalkyl of 3–7 carbon atoms,
  heterocycloalkyl of 2–6 carbon atoms and 1–2 heteroatoms selected from NH, S and O,
  aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O,
  heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O, and
  $R^4$–$R^5$,
or $R^1$ and $R^2$ combine to form, together with the nitrogen atom to which they are attached, a 5–7 membered saturated ring which may contain 1–2 additional heteroatoms selected from the group consisting of NH, $NR^8$, S and O, or combine to form, together with the nitrogen atom to which they are attached, a 5–7 membered unsaturated ring which may contain 1–2 additional heteroatoms selected from the group consisting of N, S and O,
  wherein said saturated or unsaturated ring may be substituted with 1–2 substituents selected from the group consisting of OH, alkyl of 1–6 carbon atoms, alkenyl of 2–6 carbon atoms, alkynyl of 2–6 carbon atoms, cycloalkyl of 3–7 carbon atoms, heterocycloalkyl of 2–6 carbon atoms and 1–2 heteroatoms selected from NH, S and O, halogen, haloalkyl of 1–2 carbon atoms and a number of halogen atoms up to the perhalo level, alkoxy of 1–6 carbon atoms, haloalkoxy of 1–6 carbon atoms and a number of halogen atoms up to the perhalo level, and $R^9$–$R^{10}$;

$R^3$ is selected from the group consisting of:
  hydrogen,
  alkyl of 1–8 carbon atoms,
  alkenyl of 2–8 carbon atoms,
  alkynyl of 2–8 carbon atoms,
  cycloalkyl of 3–7 carbon atoms,
  heterocycloalkyl of 2–6 carbon atoms and 1–2 heteroatoms selected from NH, S and O,
  aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O,
  heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O, and
  $R^4$–$R^5$, $R^4$ is selected from
  alkyl of 1–8 carbon atoms,
  alkenyl of 2–8 carbon atoms,
  alkynyl 2–8 carbon atoms,
  $C(=O)$,
  $S(=O)_2$, and
  $C(=O)O$—;

$R^5$ is selected from
  hydrogen,
  OH,
  alkyl of 1–8 carbon atoms,
  alkenyl 2–8 carbon atoms,
  alkynyl 2–8 carbon atoms,
  alkoxy of 1–8 carbon atoms,
  thioxy of 1–8 carbon atoms,
  aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms and heteroaryl of 4–11 carbon atoms and 1–2 heteroatoms selected from N, S and O,
  heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms and heteroaryl of 4–11 carbon atoms and 1–2 heteroatoms selected from N, S and O,
  cycloalkyl of 3–7 carbon atoms,
  heterocycloalkyl of 2–6 carbon atoms and 1–2 heteroatoms selected from NH, S and O, and
  N—$R^6$–$R^7$,
  with the proviso that $R^5$ is not OH, thioxy, alkoxy or N—$R^6$–$R^7$ when $R^4$ is $C(=O)O$—, that $R^5$ is not alkyl when $R^4$ is alkyl, alkenyl or alkynyl, and that $R^5$ is not a 6-membered heterocycloalkyl having N and O as heteroatoms when $R^4$ is $CH_2$;

$R^6$ and $R^7$ are independently selected from
  hydrogen,
  alkyl of 1–8 carbon atoms,
  alkenyl of 2–8 carbon atoms, and
  alkynyl of 2–8 carbon atoms,
  or $R^6$ and $R^7$ combine together with the nitrogen atom to which they are attached to form a 5–7 membered, unsaturated ring which may contain 1–2 additional heteroatoms selected from N, S and O or to form a 5–7 membered, saturated ring which may contain 1–2 additional heteroatoms selected from NH, $NR^{11}$, S and O;

$R^8$ is selected from
  alkyl of 1–8 carbon atoms,
  alkenyl of 2–8 carbon atoms,
  alkynyl of 2–8 carbon atoms,
  $R^{12}$–$R^{13}$,
  cycloalkyl of 3–7 carbon atoms,
  heterocycloalkyl of 2–6 carbon atoms and 1–2 heteroatoms selected from NH, S and O,
  aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O,
  heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O;

$R^9$ is selected from
  alkyl of 1–8 carbon atoms,
  alkenyl of 2–8 carbon atoms, and
  alkynyl of 2–8 carbon atoms;

$R^{10}$ is selected from
  OH,
  aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O, and heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O;

$R^{11}$ is selected from benzyl which may be substituted with
alkyl of 1–6 carbon atoms,
alkenyl of 2–6 carbon atoms,
alkynyl of 2–6 carbon atoms,
halogen, and
$R^{14}$–$R^{15}$;

$R^{12}$ is selected from
alkyl of 1–8 carbon atoms,
alkenyl of 2–8 carbon atoms, and
alkynyl of 2–8 carbon atoms;

$R^{13}$ is selected from
cycloalkyl of 3–7 carbon atoms,
heterocycloalkyl of 2–6 carbon atoms and 1–2 heteroatoms selected from NH, S and O,
aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O, and
heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O;

$R^{14}$ is alkyl of 1–3 carbon atoms;
$R^{15}$ is cylcoalkyl of 3–7 carbon atoms;
with the proviso that when $R^3$ is hydrogen,
$R^1$ and $R^2$ are independently selected from
hydrogen, with the further proviso that only one of $R^1$ and $R^2$ may be hydrogen,
$CH_2$—$CH_2$—$N(CH_2CH_3)_2$,
$CH_2$—$CH_2$—$SCH_3$,
bornyl, and

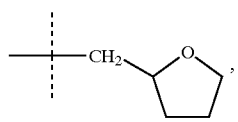, or $R^1$ and $R^2$ combine to form, together with the nitrogen atom to which they are attached, a six membered saturated ring which may contain 1–2 sulfur atoms, wherein said ring may be substituted with 1–2 substituents selected from the group consisting of alkyl of 2–8 carbon atoms, OH, $CH_2OH$, or $R^1$ and $R^2$ combine to form, together with the nitrogen atom to which they are attached, a five membered saturated ring which also contains 1–2 sulfur atoms, or $R^1$ and $R^2$ combine to form, together with the nitrogen atom to which they are attached, an 8–10 membered bicyclic saturated ring;

with the further proviso that when $R^3$ is methyl,
$R^1$ and $R^2$ are independently selected from the group consisting of
hydrogen,
alkyl of 1–8 carbon atoms,
alkenyl of 2–8 carbon atoms,
alkynyl of 2–8 carbon atoms,
cycloalkyl of 3–7 carbon atoms,
bornyl;
and pharmaceutically acceptable salts thereof.

The invention also provides methods for treating or preventing a $PDE7_B$-mediated disease or condition in a mammal. The $PDE7_B$-mediated diseases and conditions include the following: allergic and inflammatory disorders such as psoriasis, atopic dermatitis, rheumatoid arthritis, osteoarthritis, chronic bronchitis, allergic rhinitis, system lupus erythematosus, inflammatory bowel disease, pancreatitis, and multiple sclerosis, central nervous system disorders such as depression, respiratory disorders such as bronchial asthma, immune disorders, epilepsy, diabetes, diabetes-induced vascular disease, intermittent claudication, proliferative disorders such as cancer and more particularly prostate cancer, bone-related disorders such as osteoporosis and osteopenia, transplant rejection in graft v host disease, in pannus formation in rheumatoid arthritis, and restenosis.

A method of the invention therefore provides for administering to a mammal an effective amount of a compound of the formula (V):

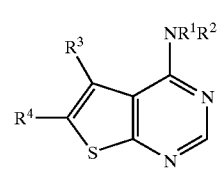

(V)

wherein
$R^1$ and $R^2$ are independently selected from the group consisting of
hydrogen,
alkyl of 1–8 carbon atoms,
alkenyl of 2–8 carbon atoms,
alkynyl of 2–8 carbon atoms,
cycloalkyl of 3–7 carbon atoms,
heterocycloalkyl of 2–6 carbon atoms and 1–2 heteroatoms selected from NH, S and O,
aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O,
heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O, and $R^5$–$R^6$, or $R^1$ and $R^2$ combine to form, together with the nitrogen atom to which they are attached, a 5–7 membered saturated ring which may contain 1–2 additional heteroatoms selected from the group consisting of NH, $NR^9$, S and O, or combine to form, together with the nitrogen atom to which they are attached, a 5–7 membered unsaturated ring which may contain 1–2 additional heteroatoms selected from the group consisting of N, S and O, wherein said saturated or unsaturated ring may be substituted with 1–2 substituents selected from the group consisting of OH, alkyl of 1–6 carbon atoms, alkenyl of 2–6 carbon atoms, alkynyl of 2–6 carbon atoms, cycloalkyl of 3–7 carbon atoms, heterocycloalkyl of 2–6 carbon atoms and 1–2 heteroatoms selected from NH, S and O, halogen, haloalkyl of 1–2 carbon atoms and a number of halogen atoms up to the perhalo level, alkoxy of 1–6 carbon atoms, haloalkoxy of 1–6 carbon atoms and a number of halogen atoms up to the perhalo level, and $R^{10}$–$R^{11}$;

$R^3$ and $R^4$ combine to form, together with the carbon atoms to which they are attached, a 5–7 membered ring containing 2–5 (—$CH_2$—) groups, 0–1

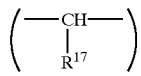

groups, and 0–2 heteroatoms selected from NH, $NR^{12}$, S and O;

$R^5$ is selected from
alkyl of 1–8 carbon atoms,
alkenyl of 2–8 carbon atoms,
alkynyl 2–8 carbon atoms,
$S(=O)_2$, and
$C(=O)O$—;

$R^6$ is selected from
hydrogen,
OH,
alkyl of 1–8 carbon atoms,
alkenyl 2–8 carbon atoms,
alkynyl 2–8 carbon atoms,
alkoxy of 1–8 carbon atoms,
thioxy of 1–8 carbon atoms,
aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms and heteroaryl of 4–11 carbon atoms and 1–2 heteroatoms selected from N, S and O,
heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms and heteroaryl of 4–11 carbon atoms and 1–2 heteroatoms selected from N, S and O,
cycloalkyl of 3–7 carbon atoms,
heterocycloalkyl of 2–6 carbon atoms and 1–2 heteroatoms selected from NH, S and O, and
N—$R^7$–$R^8$,
with the proviso that $R^6$ is not OH, thioxy, alkoxy or N—$R^7$–$R^8$ when $R^5$ is $C(=O)O$—, and with the further proviso that $R^6$ is not alkyl when $R^5$ is alkyl, alkenyl or alkynyl;

$R^7$ and $R^8$ are independently selected from
hydrogen,
alkyl of 1–8 carbon atoms,
alkenyl of 2–8 carbon atoms, and
alkynyl of 2–8 carbon atoms,
or $R^7$ and $R^8$ combine to form, together with the nitrogen atom to which they are attached, a 5–7 membered, unsaturated ring which may contain 1–2 additional heteroatoms selected from N, S and O, or combine to form, together with the nitrogen atom to which they are attached, a 5–7 membered, saturated ring which may contain 1–2 additional heteroatoms selected from NH, $NR^{11}$, S and O;

$R^9$ is selected from
alkyl of 1–8 carbon atoms,
alkenyl of 2–8 carbon atoms,
alkynyl of 2–8 carbon atoms,
$R^{13}$–$R^{14}$,
cycloalkyl of 3–7 carbon atoms,
heterocycloalkyl of 2–6 carbon atoms and 1–2 heteroatoms selected from NH, S and O,
aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O,
heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O;

$R^{10}$ is selected from
alkyl of 1–8 carbon atoms,
alkenyl of 2–8 carbon atoms, and
alkynyl of 2–8 carbon atoms;

$R^{11}$ is selected from
OH,
aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O, and heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O;

$R^{12}$ is benzyl which may be substituted with
alkyl of 1–6 carbon atoms,
alkenyl of 2–6 carbon atoms,
alkynyl of 2–6 carbon atoms,
halogen, and
$R^{15}$–$R^{16}$;

$R^{13}$ is selected from
alkyl of 1–8 carbon atoms,
alkenyl of 2–8 carbon atoms, and
alkynyl of 2–8 carbon atoms;

$R^{14}$ is selected from
cycloalkyl of 3–7 carbon atoms,
heterocycloalkyl of 2–6 carbon atoms and 1–2 heteroatoms selected from NH, S and O,
aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O, and heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O;

$R^{15}$ is alkyl of 1–3 carbon atoms;
$R^{16}$ is cylcoalkyl of 3–7 carbon atoms;
$R^{17}$ is selected from the group consisting of
hydrogen,
alkyl of 1–8 carbon atoms,
alkenyl of 2–8 carbon atoms,
alkynyl of 2–8 carbon atoms,
cycloalkyl of 3–7 carbon atoms,
heterocycloalkyl of 2–6 carbon atoms and 1–2 heteroatoms selected from NH, S and O,
aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O, heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O, and $R^5$–$R^6$;

and pharmaceutically acceptable salts thereof.

The present invention therefore provides compounds, pharmaceutical compositions containing such compounds, processes for preparing such compounds and compositions, and methods for the treatment or prevention of $PDE7_B$-mediated diseases and conditions. These and other aspects of the invention will be more apparent from the following description and claims.

DETAILED DESCRIPTION OF THE INVENTION

The invention provides novel compounds, namely 4-amino-5,6-substituted thiopheno[2,3-d]pyrimidines, pharmaceutical compositions containing such compounds, and their use for the treatment or prevention of $PDE7_B$-mediated diseases or conditions. The invention further provides methods of treating or preventing $PDE7_B$-mediated diseases or conditions in mammals, such as humans, by administration of a compound according to formula I-V, each of which has been broadly described above in the summary.

Preferred embodiments include the following:

Preferred compounds include a compound according to formula VI:

(VI)

wherein
$R^1$ and $R^2$ are independently selected from the group consisting of
hydrogen,
alkyl of 1–8 carbon atoms,
alkenyl of 2–8 carbon atoms,
alkynyl of 2–8 carbon atoms,
cycloalkyl of 3–7 carbon atoms,
heterocycloalkyl of 2–6 carbon atoms and 1–2 heteroatoms selected from NH, S and O,
aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O, heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O, and $R^4$–$R^5$, or $R^1$ and $R^2$ combine to form, together with the nitrogen atom to which they are attached, a 5–7 membered saturated ring which may contain 1–2 additional heteroatoms selected from the group consisting of NH, $NR^8$, S and O, or combine to form, together with the nitrogen atom to which they are attached, a 5–7 membered unsaturated ring which may contain 1–2 additional heteroatoms selected from the group consisting of N, S and O, wherein said saturated or unsaturated ring may be substituted with 1–2 substituents selected from the group consisting of OH, alkyl of 1–6 carbon atoms, alkenyl of 2–6 carbon atoms, alkynyl of 2–6 carbon atoms, cycloalkyl of 3–7 carbon atoms, heterocycloalkyl of 2–6 carbon atoms and 1–2 heteroatoms selected from NH, S and O, halogen, haloalkyl of 1–2 carbon atoms and a number of halogen atoms up to the perhalo level, alkoxy of 1–6 carbon atoms, haloalkoxy of 1–6 carbon atoms and a number of halogen atoms up to the perhalo level, and $R^9$–$R^{10}$;

$R^3$ is selected from the group consisting of $NR^{11}$ and $S(=O)_2$;

$R^4$ is selected from
alkyl of 1–8 carbon atoms,
alkenyl of 2–8 carbon atoms,
alkynyl 2–8 carbon atoms,
C(=O), and
$S(=O)_2$;

$R^5$ is selected from
hydrogen,
OH,
alkyl of 1–8 carbon atoms,
alkenyl 2–8 carbon atoms,
alkynl 2–8 carbon atoms,
alkoxy of 1–8 carbon atoms,
thioxy of 1–8 carbon atoms,
aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms and heteroaryl of 4–11 carbon atoms and 1–2 heteroatoms selected from N, S and O, heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms and heteroaryl of 4–11 carbon atoms and 1–2 heteroatoms selected from N, S and O, cycloalkyl of 3–7 carbon atoms, heterocycloalkyl of 2–6 carbon atoms and 1–2 heteroatoms selected from NH, S and O, and

N—$R^6$–$R^7$, with the proviso that $R^5$ is not alkyl when $R^4$ is alkyl, alkenyl or alkynyl;

$R^6$ and $R^7$ are independently selected from
hydrogen,
alkyl of 1–8 carbon atoms,
alkenyl of 2–8 carbon atoms, and
alkynyl of 2–8 carbon atoms, or $R^6$ and $R^7$ combine together with the nitrogen atom to which they are attached to form a 5–7 membered, unsaturated ring which may contain 1–2 additional heteroatoms selected from N, S and O or to form a 5–7 membered, saturated ring which may contain 1–2 additional heteroatoms selected from NH, $NR^{11}$, S and O;

$R^8$ is selected from
alkyl of 1–8 carbon atoms,
alkenyl of 2–8 carbon atoms,
alkynyl of 2–8 carbon atoms,
$R^{12}$–$R^{13}$,
cycloalkyl of 3–7 carbon atoms,
heterocycloalkyl of 2–6 carbon atoms and 1–2 heteroatoms selected from NH, S and O,
aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O, heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O;

$R^9$ is selected from
alkyl of 1–8 carbon atoms,
alkenyl of 2–8 carbon atoms, and
alkynyl of 2–8 carbon atoms;

$R^{10}$ is selected from
OH,
aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O, and heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O;

$R^{11}$ is benzyl which may be substituted with an unbranched alkyl of 2–6 carbon atoms, alkenyl of 2–6 carbon atoms, alkynyl of 2–6 carbon atoms, and $R^{14}$–$R^{15}$;

$R^{12}$ is selected from
alkyl of 1–8 carbon atoms,
alkenyl of 2–8 carbon atoms, and
alkynyl of 2–8 carbon atoms;

$R^{13}$ is selected from
cycloalkyl of 3–7 carbon atoms,
heterocycloalkyl of 2–6 carbon atoms and 1–2 heteroatoms selected from NH, S and O,
aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O, and
heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O;

or $R^1$ and $R^2$ combine to form, together with the nitrogen atom to which they are attached, a 5–7 membered saturated ring or a 8–10 membered bicyclic saturated ring;

$R^{14}$ is alkyl of 1–3 carbon atoms;
$R^{15}$ is cylcoalkyl of 3–7 carbon atoms;
and pharmaceutically acceptable salts thereof.

Another preferred embodiment is a compound according to formula VII:

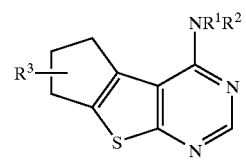

(VII)

wherein
$R^1$ and $R^2$ are independently selected from the group consisting of
hydrogen,
alkyl of 1–8 carbon atoms,
alkenyl of 2–8 carbon atoms,
alkynyl of 2–8 carbon atoms,
cycloalkyl of 3–7 carbon atoms,
heterocycloalkyl of 2–6 carbon atoms and 1–2 heteroatoms selected from NH, S and O,
aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O,
heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O, and
$R^4$–$R^5$, or $R^1$ and $R^2$ combine to form, together with the nitrogen atom to which they are attached, a 5–7 membered saturated ring which may contain 1–2 additional heteroatoms selected from the group consisting of NH, $NR^8$, S and O, or combine to form, together with the nitrogen atom to which they are attached, a 5–7 membered unsaturated ring which may contain 1–2 additional heteroatoms selected from the group consisting of N, S and O,
wherein said saturated or unsaturated ring may be substituted with 1–2 substituents selected from the group consisting of OH, alkyl of 1–6 carbon atoms, alkenyl of 2–6 carbon atoms, alkynyl of 2–6 carbon atoms, cycloalkyl of 3–7 carbon atoms, heterocylcoalkyl of 2–6 carbon atoms and 1–2 heteroatoms selected from NH, S and O, halogen, haloalkyl of 1–2 carbon atoms and a number of halogen atoms up to the perhalo level, alkoxy of 1–6 carbon atoms, haloalkoxy of 1–6 carbon atoms and a number of halogen atoms up to the perhalo level, and $R^9$–$R^{10}$;

$R^3$ is selected from the group consisting of:
hydrogen,
alkyl of 1–8 carbon atoms,
alkenyl of 2–8 carbon atoms, alkynyl of 2–8 carbon atoms,
cycloalkyl of 3–7 carbon atoms,
heterocycloalkyl of 2–6 carbon atoms and 1–2 heteroatoms selected from NH, S and O,
aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O,
heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O, and
$R^4$–$R^5$;
$R^4$ is selected from
alkyl of 1–8 carbon atoms,
alkenyl of 2–8 carbon atoms,
alkynyl 2–8 carbon atoms,
C(=O), and
S(=O)$_2$;
$R^5$ is selected from
hydrogen,
OH,
alkyl of 1–8 carbon atoms,
alkenyl 2–8 carbon atoms,
alkynyl 2–8 carbon atoms,
alkoxy of 1–8 carbon atoms,
thioxy of 1–8 carbon atoms,
aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms and heteroaryl of 4–11 carbon atoms and 1–2 heteroatoms selected from N, S and O,
heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms and heteroaryl of 4–11 carbon atoms and 1–2 heteroatoms selected from N, S and O,
cycloalkyl of 3–7 carbon atoms,
heterocycloalkyl of 2–6 carbon atoms and 1–2 heteroatoms selected from
NH, S and O, and
N—$R^6$–$R^7$,
with the proviso that $R^5$ is not alkyl when $R^4$ is alkyl, alkenyl or alkynyl;

$R^6$ and $R^7$ are independently selected from
hydrogen,
alkyl of 1–8 carbon atoms,
alkenyl of 2–8 carbon atoms, and
alkynyl of 2–8 carbon atoms,
or $R^6$ and $R^7$ combine together with the nitrogen atom to which they are attached to form a 5–7 membered, unsaturated ring which may contain 1–2 additional heteroatoms selected from N, S and O or to form a 5–7 membered, saturated ring which may contain 1–2 additional heteroatoms selected from NH, $NR^{11}$, S and O;
$R^8$ is selected from
alkyl of 1–8 carbon atoms,
alkenyl of 2–8 carbon atoms,
alkynyl of 2–8 carbon atoms,
$R^{12}$–$R^{13}$,
cycloalkyl of 3–7 carbon atoms,
heterocycloalkyl of 2–6 carbon atoms and 1–2 heteroatoms selected from NH, S and O,
aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O,
heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O;
$R^9$ is selected from
alkyl of 1–8 carbon atoms,
alkenyl of 2–8 carbon atoms, and
alkynyl of 2–8 carbon atoms;
$R^{10}$ is selected from
OH,
aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O, and
heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O;

$R^{11}$ is benzyl which may be substituted with
alkyl of 1–6 carbon atoms,
alkenyl of 2–6 carbon atoms,
alkynyl of 2–6 carbon atoms,
halogen, and
$R^{14}$–$R^{15}$;

$R^{12}$ is selected from
alkyl of 1–8 carbon atoms,
alkenyl of 2–8 carbon atoms, and
alkynyl of 2–8 carbon atoms;

$R^{13}$ is selected from
cycloalkyl of 3–7 carbon atoms,
heterocycloalkyl of 2–6 carbon atoms and 1–2 heteroatoms selected from NH, S and O,
aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O, and
heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, alkyl of 6–12 carbon atoms or heteroaryl of 4–11 carbon atoms and 1–2 heteroatoms selected from N, S and O;

$R^{14}$ is alkyl of 1–3 carbon atoms;

$R^{15}$ is cylcoalkyl of 3–7 carbon atoms;

with the proviso that when $R^3$ is hydrogen,
$R^1$ and $R^2$ are independently selected from the group consisting of
hydrogen, with the further proviso that $R^1$ and $R^2$ are not both hydrogen,
alkyl of 3–8 carbon atoms,
alkenyl of 2–8 carbon atoms,
alkynyl of 2–8 carbon atoms,
heterocycloalkyl of 4–6 carbon atoms and 1–2 heteroatoms selected from NH, S
and O, and
bornyl,
or $R^1$ and $R^2$ combine to form, together with the nitrogen atom to which they are attached,
a 5–7 membered saturated ring which contains 1–2 sulfur atoms, or
an 8–10 membered bicyclic saturated ring;
and pharmaceutically acceptable salts thereof.

Another preferred embodiment includes a compound according to formula VIII:

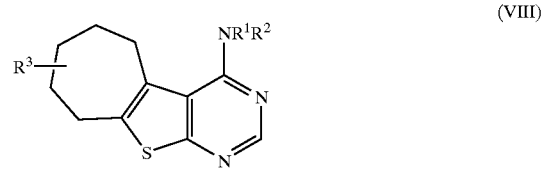

(VIII)

wherein
$R^1$ and $R^2$ are independently selected from the group consisting of
hydrogen,
alkyl of 1–8 carbon atoms,
alkenyl of 2–8 carbon atoms,
alkynyl of 2–8 carbon atoms,
alkoxy of 1–8 carbon atoms,
cycloalkyl of 3–7 carbon atoms,
heterocycloalkyl of 2–6 carbon atoms and 1–2 heteroatoms selected from NH, S and O,
aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O,
heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O, and
$R^4$–$R^5$,
or $R^1$ and $R^2$ combine to form, together with the nitrogen atom to which they are attached, a 5–7 membered saturated ring which may contain 1–2 additional heteroatoms selected from the group consisting of NH, $NR^8$, S and O, or combine to form, together with the nitrogen atom to which they are attached, a 5–7 membered unsaturated ring which may contain 1–2 additional heteroatoms selected from the group consisting of N, S and O,
wherein said saturated or unsaturated ring may be substituted with 1–2 substituents selected from the group consisting of OH, alkyl of 1–6 carbon atoms, alkenyl of 2–6 carbon atoms, alkynyl of 2–6 carbon atoms, cycloalkyl of 3–7 carbon atoms, heterocylcoalkyl of 2–6 carbon atoms and 1–2 heteroatoms selected from NH, S and O, halogen, haloalkyl of 1–2 carbon atoms and a number of halogen atoms up to the perhalo level, alkoxy of 1–6 carbon atoms, haloalkoxy of 1–6 carbon atoms and a number of halogen atoms up to the perhalo level, and $R^9$–$R^{10}$;

$R^3$ is selected from the group consisting of:
hydrogen,
alkyl of 1–8 carbon atoms,
alkenyl of 2–8 carbon atoms,
alkynyl of 2–8 carbon atoms, cycloalkyl of 3–7 carbon atoms,
heterocycloalkyl of 2–6 carbon atoms and 1–2 heteroatoms selected from NH, S and O,
aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O,
heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O, and
$R^4$–$R^5$,
$R^4$ is selected from
alkyl of 1–8 carbon atoms,
alkenyl of 2–8 carbon atoms,
alkynyl 2–8 carbon atoms,
C(=O), and
S(=O)$_2$;
$R^5$ is selected from
hydrogen,
OH,
alkyl of 1–8 carbon atoms,
alkenyl 2–8 carbon atoms,
alkynyl 2–8 carbon atoms,
alkoxy of 1–8 carbon atoms,
thioxy of 1–8 carbon atoms,
aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms and heteroaryl of 4–11 carbon atoms and 1–2 heteroatoms selected from N, S and O,
heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms and heteroaryl of 4–11 carbon atoms and 1–2 heteroatoms selected from N, S and O,
cycloalkyl of 3–7 carbon atoms,
heterocycloalkyl of 2–6 carbon atoms and 1–2 heteroatoms selected from
NH, S and O, and
N—$R^6$–$R^7$,
with the proviso that $R^5$ is not alkyl when $R^4$ is alkyl, alkenyl or alkynyl;

$R^6$ and $R^7$ are independently selected from
hydrogen,
alkyl of 1–8 carbon atoms,
alkenyl of 2–8 carbon atoms, and
alkynyl of 2–8 carbon atoms,
or $R^6$ and $R^7$ combine together with the nitrogen atom to which they are attached to form a 5–7 membered, unsaturated ring which may contain 1–2 additional heteroatoms selected from N, S and O or to form a 5–7 membered, saturated ring which may contain 1–2 additional heteroatoms selected from NH, $NR^{11}$, S and O;
$R^8$ is selected from
alkyl of 1–8 carbon atoms,
alkenyl of 2–8 carbon atoms,
alkynyl of 2–8 carbon atoms,
$R^{12}$–$R^{13}$,
cycloalkyl of 3–7 carbon atoms,
heterocycloalkyl of 2–6 carbon atoms and 1–2 heteroatoms selected from NH, S and O,
aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O,
heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O;
$R^9$ is selected from
alkyl of 1–8 carbon atoms,
alkenyl of 2–8 carbon atoms, and
alkynyl of 2–8 carbon atoms;
$R^{10}$ is selected from
OH,
aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O, and
heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O;

$R^{11}$ is benzyl which may be substituted with
alkyl of 1–6 carbon atoms,
alkenyl of 2–6 carbon atoms,
alkynyl of 2–6 carbon atoms,
halogen, and
$R^{14}$–$R^{15}$;

$R^{12}$ is selected from
alkyl of 1–8 carbon atoms,
alkenyl of 2–8 carbon atoms, and
alkynyl of 2–8 carbon atoms;

$R^{13}$ is selected from
cycloalkyl of 3–7 carbon atoms,
heterocycloalkyl of 2–6 carbon atoms and 1–2 heteroatoms selected from NH, S and O,
aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O, and
heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O;

$R^{14}$ is alkyl of 1–3 carbon atoms;
$R^{15}$ is cylcoalkyl of 3–7 carbon atoms;
with the proviso that when $R^3$ is hydrogen,
$R^1$ and $R^2$ are independently selected from the group consisting of
hydrogen, with the further proviso that only one of $R^1$ and $R^2$ may be hydrogen,
alkyl of 1–8 carbon atoms,
alkenyl of 2–8 carbon atoms,
alkynl of 2–8 carbon atoms,
alkoxy of 1–8 carbon atoms, cycloalkyl of 3–7 carbon atoms, and
phenyl which may be substituted from one to five times with bromine, chlorine, $CH_3$, or $CF_3$;

or $R^1$ and $R^2$ combine to form, together with the nitrogen atom to which they are attached, a 6–7 membered saturated ring which may contain 1–2 additional heteroatoms selected from the group consisting of NH, $NR^8$, S, and O, or combine to form, together with the nitrogen atom to which they are attached, a 6–7 membered unsaturated ring which may contain 1–2 additional heteroatoms selected from the group consisting of N, S and O,
wherein said saturated or unsaturated ring may be substituted with 1–2 substituents selected from the group consisting of OH, alkyl of 1–6 carbon atoms, alkenyl of 2–6 carbon atoms, alkynyl of 2–6 carbon atoms, cycloalkyl of 3–7 carbon atoms, heterocylcoalkyl of 2–6 carbon atoms and 1–2 heteroatoms selected from NH, S and O, halogen, haloalkyl of 1–2 carbon atoms and a number of halogen atoms up to the perhalo level, alkoxy of 1–6 carbon atoms, haloalkoxy of 1–6 carbon atoms and a number of halogen atoms up to the perhalo level, and $R^9$–$R^{10}$;

and pharmaceutically acceptable salts thereof.

A further preferred embodiment includes a compound according to the formula IX:

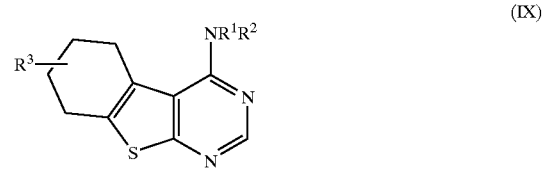

(IX)

wherein
$R^1$ and $R^2$ are independently selected from the group consisting of
hydrogen,
alkyl of 1–8 carbon atoms,
alkenyl of 2–8 carbon atoms,
alkynyl of 2–8 carbon atoms,
cycloalkyl of 3–7 carbon atoms,
heterocycloalkyl of 2–6 carbon atoms and 1–2 heteroatoms selected from NH, S and O,
aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O,
heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O, and
$R^4$–$R^5$,
or $R^1$ and $R^2$ combine to form, together with the nitrogen atom to which they are attached, a 5–7 membered saturated ring which may contain 1–2 additional heteroatoms selected from the group consisting of NH, $NR^8$, S and O, or combine to form, together with the nitrogen atom to which they are attached, a 5–7 membered unsaturated ring which may contain 1–2 additional heteroatoms selected from the group consisting of N, S and O,
wherein said saturated or unsaturated ring may be substituted with 1–2 substituents selected from the group consisting of OH, alkyl of 1–6 carbon atoms, alkenyl of 2–6 carbon atoms, alkynyl of 2–6 carbon atoms, cycloalkyl of 3–7 carbon atoms, heterocylcoalkyl of 2–6 carbon atoms and 1–2 heteroatoms selected from NH, S and O, halogen, haloalkyl of 1–2 carbon atoms and a number of halogen atoms up to the perhalo level, alkoxy of 1–6 carbon atoms, haloalkoxy of 1–6 carbon atoms and a number of halogen atoms up to the perhalo level, and $R^9$–$R^{10}$;

$R^3$ is selected from the group consisting of:
  alkyl of 2–8 carbon atoms,
  alkenyl of 2–8 carbon atoms,
  alkynyl of 2–8 carbon atoms,
  cycloalkyl of 3–7 carbon atoms,
  heterocycloalkyl of 2–6 carbon atoms and 1–2 heteroatoms selected from NH, S and O,
  aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O,
  heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O, and
  $R^4$–$R^5$,
$R^4$ is selected from
  alkyl of 2–8 carbon atoms,
  alkenyl of 2–8 carbon atoms,
  alkynyl 2–8 carbon atoms,
  C(=O), and
  S(=O)$_2$;
$R^5$ is selected from
  hydrogen,
  OH,
  alkyl of 1–8 carbon atoms,
  alkenyl 2–8 carbon atoms,
  alkynyl 2–8 carbon atoms,
  alkoxy of 1–8 carbon atoms,
  thioxy of 1–8 carbon atoms,
  aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms and heteroaryl of 4–11 carbon atoms and 1–2 heteroatoms selected from N, S and O,
  heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms and heteroaryl of 4–11 carbon atoms and 1–2 heteroatoms selected from N, S and O,
  cycloalkyl of 3–7 carbon atoms,
  heterocycloalkyl of 2–6 carbon atoms and 1–2 heteroatoms selected from NH, S and O, and
  N—$R^6$–$R^7$;
$R^6$ and $R^7$ are independently selected from
  hydrogen,
  alkyl of 1–8 carbon atoms,
  alkenyl of 2–8 carbon atoms, and
  alkynyl of 2–8 carbon atoms,
  or $R^6$ and $R^7$ combine together with the nitrogen atom to which they are attached to form a 5–7 membered, unsaturated ring which may contain 1–2 additional heteroatoms selected from N, S and O or to form a 5–7 membered, saturated ring which may contain 1–2 additional heteroatoms selected from NH, $NR^1$, S and O;
$R^8$ is selected from
  alkyl of 1–8 carbon atoms,
  alkenyl of 2–8 carbon atoms,
  alkynyl of 2–8 carbon atoms,
  $R^{12}$–$R^{13}$,
  cycloalkyl of 3–7 carbon atoms,
  heterocycloalkyl of 2–6 carbon atoms and 1–2 heteroatoms selected from NH, S and O,
  aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O,
  heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O;
$R^9$ is selected from
  alkyl of 1–8 carbon atoms,
  alkenyl of 2–8 carbon atoms, and
  alkynyl of 2–8 carbon atoms;
$R^{10}$ is selected from
  OH,
  aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O, and
  heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O;

$R^{11}$ is selected from benzyl which may be substituted with
- alkyl of 1–6 carbon atoms,
- alkenyl of 2–6 carbon atoms,
- alkynyl of 2–6 carbon atoms,
- halogen, and
- $R^{14}-R^{15}$;

$R^{12}$ is selected from
- alkyl of 1–8 carbon atoms,
- alkenyl of 2–8 carbon atoms, and
- alkynyl of 2–8 carbon atoms;

$R^{13}$ is selected from
- cycloalkyl of 3–7 carbon atoms,
- heterocycloalkyl of 2–6 carbon atoms and 1–2 heteroatoms selected from NH, S and O,
- aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O, and
- heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O;

$R^{14}$ is alkyl of 1–3 carbon atoms; and
$R^{15}$ is cylcoalkyl of 3–7 carbon atoms;
and pharmaceutically acceptable salts thereof.

As used herein, the term "aryl" includes aromatic ring structures that are substituents on another atom. These aryls may also be substituted with substituents, such as nitrile, nitro, halogen, haloalkyl, etc. Non-limiting examples of aryls include phenyl, napthyl, etc. Likewise, the term "heteroaryl" as used herein includes aromatic ring structures containing between one and three heteroatoms, such as O, N and S, that are substituents on another atom. These heteroaryls may also be substituted with substituents, such as nitrile, nitro, halogen, haloalkyl, etc. Non-limiting examples of heteroaryls include pyridyl, furyl, quinolyl, etc.

As used herein the term "alkyl" includes straight-chain or branched alkyls of between 1 and 8 carbon atoms. The term "alkenyl" includes straight-chain or branched alkenyls of between 2 and 8 carbon atoms. As used herein the term "alkynyl" includes straight-chain or branched alkynyls of between 2 and 8 carbon atoms. As used herein, "benzyl substituted" with a substituent includes benzyl having one or more substituents on the alkyl or phenyl carbons.

Compounds of formulas I–IX may be useful in the treatment or prevention of $PDE7_B$-mediated diseases or conditions. An agent that binds to $PDE7_B$ may be employed for a wide variety of indications, including the following: allergic and inflammatory disorders such as psoriasis, atopic dermatitis, rheumatoid arthritis, osteoarthritis, chronic bronchitis, allergic rhinitis, system lupus erythematosus, inflammatory bowel disease, pancreatitis, and multiple sclerosis, central nervous system disorders such as depression, respiratory disorders such as bronchial asthma, immune disorders, epilepsy, diabetes, diabetes-induced vascular disease, intermittent claudication, proliferative disorders such as cancer and more particularly prostate cancer, osteoporosis, osteopenia, transplant rejection in graft v host disease, in pannus formation in rheumatoid arthritis, and restenosis.

Compounds of formulas I–IX are preferably used in the treatment or prevention of osteopenia, osteoporosis, and respiratory disorders such as asthma.

$PDE7_B$ has been shown to be a cAMP specific PDE. Thus, it is possible that any disease or condition involving a pathway in which cAMP is a signaling molecule may be treated or prevented by administration of a $PDE7_B$ inhibitor, such as those of Formula I. For example, cAMP regulation has been suggested as a means to control inflammation (Moore, A. R. et al. (1995) *Clin. Exp. Immunol.* 101: 387–389). cAMP is rapidly broken down by PDEs. Because hydrolysis of cAMP is not dependent upon a single PDE but on a range of isoenzymes that differ in their tissue distribution, therapeutic use of specific PDE inhibitors is believed possible for specific ailments without unacceptable systemic side effects (Moore, A. R. et al. supra). Another example involves T cell-dependent disorders. Selectively reducing PDE7 expression with a PDE7 antisense oligonucleotide inhibited T cell proliferation (Li, Linsong et al. (1999) *Science* 283: 848–849). Increased PDE7 in T cells correlated with decreased cAMP leading to increased proliferation.

PDE4 has also been shown to be a cAMP-specific PDE. It is believed that disorders associated with PDE4 activity may also be treated or prevented by compounds that modulate PDE7 activity because of the similar cAMP-specificity of the two enzymes. For example, osteoporosis has been associated with PDE4 activity (Kasugai, S. et al. (1999) *Drug News Perspect.* 12(9); 529–534). Two known medicaments for treating osteoporosis were studied, and their effects were determined to be mainly mediated by an increase in cAMP level. Since PDE4 specifically degrades cAMP, PDE4 inhibitors were added to the tissue system and resulted in increased bone-like tissue formation. When the inhibitors were administered to mice and rats, increased bone mass was seen. In other work on osteoporosis using murine models, administration of two PDE inhibitors was shown to significantly increase both cortical and cancellous bone mass (Kinoshita, T. et al. (2000) *Bone* 27(6): 811817). The administration of either pentoxifylline, an inhibitor of cAMP PDEs, or rolipram, an inhibitor specific to PDE4, in normal mice significantly increased both cortical and cancellous bone mass. Denbufylline, another selective inhibitor of PDE4, was shown to inhibit the decrease in the bone mineral density of femurs from Walker 256/S-bearing rats without influence on healthy rats (Miyamota, K. et al. (1997) *Biochem. Pharmacol.* 54: 613617). These studies strongly suggest a role for inhibitors of cAMP-selective PDEs in treatment and prevention of osteoporosis.

The present invention also includes pharmaceutically acceptable salts of the compounds of Formulas I–IX. Suitable pharmaceutically acceptable salts are well known to those skilled in the art and include basic salts of inorganic and organic acids, such as hydrochloric acid, hydrobromic acid, sulphuric acid, phosphoric acid, methanesulphonic acid, trifluoromethanesulfonic acid, sulphonic acid, acetic acid, trifluoroacetic acid, malic acid, tartaric acid, citric acid, lactic acid, oxalic acid, succinic acid, fumaric acid, maleic acid, benzoic acid, salicylic acid, phenylacetic acid, and mandelic acid. In addition, pharmaceutically acceptable salts include acid salts of inorganic bases, such as salts containing alkaline cations (e.g., $Li^+$ $Na^+$ or $K^+$), alkaline earth cations (e.g., $Mg^{+2}$, $Ca^{+2}$ or $Ba^{+2}$), the ammonium cation, as well as acid salts of organic bases, including aliphatic and aromatic substituted ammonium, and quaternary ammonium cations such as those arising from protonation or peralkylation of triethylamine, N,N-diethylamine, N,N-dicyclohexylamine, pyridine, N,N-dimethylaminopyridine (DMAP), 1,4-diazabicyclo[2.2.2]octane (DABCO), 1,5-diazabicyclo[4.3.0]non-5-ene (DBN) and 1,8-diazabicyclo[5.4.0]undec-7-ene (DBU).

A number of the compounds of Formulas I–IX possess asymmetric carbons and can therefore exist in racemic and optically active forms. Methods of separation of enantiomeric and diastereomeric mixtures are well known to the skilled in the art. The present invention encompasses any racemic or optically active forms of compounds described in Formulas I–IX which possess $PDE7_B$ binding activity or the use of any racemic or optically active forms of compounds described in Formulas I–IX for the treatment or prevention of $PDE7_B$-mediated diseases or conditions.

The therapeutic agents of the invention may be employed alone or concurrently with other therapies. For example, they may be used for the treatment of osteoporosis or osteopenia in combination with a calcium source, vitamin D or analogues of vitamin D, and/or antiresorptive therapies such as estrogen replacement therapy, treatment with a fluoride source, treatment with calcitonin or a calcitonin analogue, or treatment with a bisphosphonate such as alendronate. The agent may be used with therapies such as estrogen replacement therapy. The agent may be used concurrently with therapies such as estrogen replacement therapy and/or a gonadotropin-releasing hormone agonist. Finally, the agent may be used concurrently with therapies such as an androgen.

Therapeutic agents of the invention may be employed for the treatment of asthma and other respiratory disorders in combination with other known asthma therapies, such as in combination with steroids, non-steroidal anti-inflammatory agents, and/or non-narcotic analgesics.

The method of the invention is intended to be employed for treatment of $PDE7_B$-mediated diseases or conditions in both humans and other mammals.

The compounds may be administered orally, dermally, parenterally, by injection, by inhalation or spray, or sublingually, rectally or vaginally in dosage unit formulations. The term 'administered by injection' includes intravenous, intraarticular, intramuscular, subcutaneous and parenteral injections, as well as use of infusion techniques. Dermal administration may include topical application or transdermal administration. One or more compounds may be present in association with one or more non-toxic pharmaceutically acceptable carriers and, if desired, other active ingredients.

Compositions intended for oral use may be prepared according to any suitable method known to the art for the manufacture of pharmaceutical compositions. Such compositions may contain one or more agents selected from the group consisting of diluents, sweetening agents, flavoring agents, coloring agents and preserving agents in order to provide palatable preparations.

Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; and binding agents, for example magnesium stearate, stearic acid or talc. The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed. These compounds may also be prepared in solid, rapidly released form.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions containing the active materials in admixture with excipients suitable for the manufacture of aqueous suspensions may also be used. Such excipients are suspending agents, for example sodium carboxymethylcellulose, methylcellulose, hydroxypropyl-methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

The compounds may also be in the form of non-aqueous liquid formulations, e.g., oily suspensions which may be formulated by suspending the active ingredients in a vegetable oil, for example arachis oil, olive oil, sesame oil or peanut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Pharmaceutical compositions of the invention may also be in the form of oil-in-water emulsions. The oil phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The compounds may also be administered in the form of suppositories for rectal or vaginal administration of the drug. These compositions can be prepared by mixing the drug with a suitable non-irritating excipient which is solid at ordinary temperatures but liquid at the rectal or vaginal temperature and will therefore melt in the rectum or vagina to release the drug. Such materials include cocoa butter and polyethylene glycols.

Compounds of the invention may also be administered transdermally using methods known to those skilled in the art (see, for example: Chien; "Transdermal Controlled Systemic Medications"; Marcel Dekker, Inc.; 1987. Lipp et al. WO 94/04157 Mar 3, 1994). For example, a solution or suspension of a compound of Formula I in a suitable volatile solvent optionally containing penetration enhancing agents can be combined with additional additives known to those skilled in the art, such as matrix materials and bacteriocides. After sterilization, the resulting mixture can be formulated following known procedures into dosage forms. In addition, on treatment with emulsifying agents and water, a solution or suspension of a compound of Formula I may be formulated into a lotion or salve.

Suitable solvents for processing transdermal delivery systems are known to those skilled in the art, and include lower alcohols such as ethanol or isopropyl alcohol, lower ketones such as acetone, lower carboxylic acid esters such as ethyl acetate, polar ethers such as tetrahydrofuran, lower hydrocarbons such as hexane, cyclohexane or benzene, or halogenated hydrocarbons such as dichloromethane, chloroform, trichlorotrifluoroethane, or trichlorofluoroethane. Suitable solvents may also include mixtures one or more materials selected from lower alcohols, lower ketones, lower carboxylic acid esters, polar ethers, lower hydrocarbons, halogenated hydrocarbons.

Suitable penetration enhancing materials for transdermal delivery systems are known to those skilled in the art, and include, for example, monohydroxy or polyhydroxy alcohols such as ethanol, propylene glycol or benzyl alcohol, saturated or unsaturated $C_8$–$C_{18}$ fatty alcohols such as lauryl alcohol or cetyl alcohol, saturated or unsaturated $C_8$–$C_{18}$ fatty acids such as stearic acid, saturated or unsaturated fatty esters with up to 24 carbons such as methyl, ethyl, propyl, isopropyl, n-butyl, sec-butyl isobutyl tert-butyl or monoglycerin esters of acetic acid, capronic acid, lauric acid, myristinic acid, stearic acid, or palmitic acid, or diesters of saturated or unsaturated dicarboxylic acids with a total of up to 24 carbons such as diisopropyl adipate, diisobutyl adipate, diisopropyl sebacate, diisopropyl maleate, or diisopropyl fumarate. Additional penetration enhancing materials include phosphatidyl derivatives such as lecithin or cephalin, terpenes, amides, ketones, ureas and their derivatives, and ethers such as dimethyl isosorbid and diethyleneglycol monoethyl ether. Suitable penetration enhancing formulations may also include mixtures one or more materials selected from monohydroxy or polyhydroxy alcohols, saturated or unsaturated $C_8$–$C_{18}$ fatty alcohols, saturated or unsaturated $C_8$–$C_{18}$ fatty acids, saturated or unsaturated fatty esters with up to 24 carbons, diesters of saturated or unsaturated dicarboxylic acids with a total of up to 24 carbons, phosphatidyl derivatives, terpenes, amides, ketones, ureas and their derivatives, and ethers.

Suitable binding materials for transdermal delivery systems are known to those skilled in the art and include polyacrylates, silicones, polyurethanes, block polymers, styrene-butadiene copolymers, and natural and synthetic rubbers. Cellulose ethers, derivatized polyethylenes, and silicates may also be used as matrix components. Additional additives, such as viscous resins or oils may be added to increase the viscosity of the matrix.

For all regimens of use disclosed herein for compounds of Formulas I–9, the daily oral dosage regimen will preferably be from 0.01 to 200 mg/Kg of total body weight. The daily dosage for administration by injection, including intravenous, intramuscular, subcutaneous and parenteral injections, and use of infusion techniques will preferably be from 0.01 to 200 mg/Kg of total body weight. The daily rectal dosage regimen will preferably be from 0.01 to 200 mg/Kg of total body weight. The daily vaginal dosage regimen will preferably be from 0.01 to 200 mg/Kg of total body weight. The daily topical dosage regimen will preferably be from 0.1 to 200 mg administered between one to four times daily. The transdermal concentration will preferably be that required to maintain a daily dose of from 0.01 to 200 mg/Kg. The daily inhalation dosage regimen will preferably be from 0.01 to 10 mg/Kg of total body weight.

It will be appreciated by those skilled in the art that the particular method of administration will depend on a variety of factors, all of which are considered routinely when administering therapeutics. It will also be understood, however, that the specific dose level for any given patient will depend upon a variety of factors, including, but not limited to the activity of the specific compound employed, the age of the patient, the body weight of the patient, the general health of the patient, the gender of the patient, the diet of the patient, time of administration, route of administration, rate of excretion, drug combinations, and the severity of the condition undergoing therapy. It will be further appreciated by one skilled in the art that the optimal course of treatment, ie., the mode of treatment and the daily number of doses of a compound of Formula I or a pharmaceutically acceptable salt thereof given for a defined number of days, can be ascertained by those skilled in the art using conventional treatment tests.

The entire disclosures of all applications, patents and publications cited above and below are hereby incorporated by reference.

The compounds of Formulas I–IX may be prepared by use of known chemical reactions and procedures, from known compounds (or from starting materials which, in turn, are producible from known compounds) through the preparative methods shown below as well as by other reactions and procedures known to the skilled in the art. Nevertheless, the following general preparative methods are presented to aid practitioners in synthesizing the compounds of the invention, with more detailed particular examples being presented in the experimental section. The examples are for illustrative purposes only and are not intended, nor should they be construed, to limit the invention in any way.

For example, compounds of Formulas I–IX may be conveniently prepared by the scheme shown below, in which the $R^1$–$R^4$ groups have the meaning described above:

Scheme I

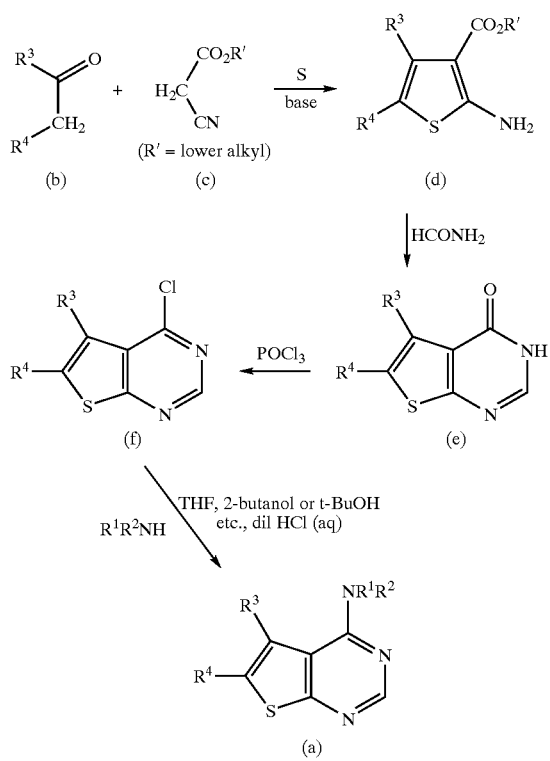

The aminothiophene esters of formula (d) are either commercially available (e.g., see ACROS Organics, Cat #A007199501) or may be prepared by reaction of a cyanoacetic ester of formula (c) with a ketone such as cyclopentanone in the presence of powdered sulfur and a base such as diethylamine at room temperature or with mild heating. The formula (d) esters may then be converted to the formula (e) thienopyrimidones by reaction with neat formamide while heating up to reflux, preferably about 190° C. Heating the formula (e) thienopyrimidone phosphorous oxychloride provides the chlorothienopyrimidine intermediate of formula (f). Finally, the desired formula I compounds may be prepared by reaction of (f) with a variety of amines of formula $R_1R_2NH$ carried out in the presence of a catalytic amount of dilute aqueous acid, such as 1% HCl, either in a protic solvent, such as 2-butanol or t-butanol, or in THF. The reaction may be conducted in conventional means by warming the mixture up to reflux, or by parallel (combinatorial) synthesis by warming individual sealed vials containing the reactants, catalyst and solvent to about 80° C.

Using this method, and starting with a variety of compounds of formula (f) and amines, a large number of compounds of formula (a) may be prepared and tested for biological activity.

Abbreviations and Acronyms

When the following abbreviations are used herein, they have the following meaning:

| | |
|---|---|
| Ac$_2$O | acetic anhydride |
| anhy | anhydrous |
| Celite ® | diatomaceous earth filter agent, ® Celite Corp. |
| CI-MS | chemical ionization mass spectroscopy |
| conc | concentrated |
| DME | dimethoxyethane |
| DMF | N,N-dimethylformamide |
| DMSO | dimethylsulfoxide |
| EtOAc | ethyl acetate |
| EtOH | ethanol (100%) |
| Et$_2$O | diethyl ether |
| Et$_3$N | triethylamine |
| Extrelut ® NT | diatomaceous earth filter agent, ® Merck KgaA, Darmstadt, Germany |
| HPLC | high performance liquid chromatography |
| HPLC ES-MS | high performance liquid chromatography-electrospray mass spectroscopy |
| MeOH | methanol |
| MS | Mass Spectroscopy |
| pet ether | petroleum ether |
| rt | room temperature |
| satd | saturated |
| THF | tetrahydrofuran |
| TLC | thin layer chromatography |
| Ts | Tosyl |

EXAMPLE 1

Preparation of Ethyl 2-amino-5,6-dihydro-4H-cyclopenta[b]thiophene-3-carboxylate

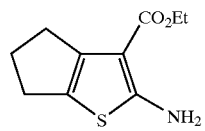

To a solution of cyclopentanone (20 g, 0.238) and ethyl cyanoacetate (26.9 g, 0.25 mol) in 80 mL ethanol was added powdered sulfur (8.0 g, 0.25 mol) while stirring under argon. To this mixture was added 17.4 g diethylamine (0.238 mol) dropwise over 25 min via addition funnel and the mixture was stirred for 3 h at rt. The solvent was removed and residue was then partitioned between 60 mL of water and 60 mL of ethyl acetate. The organic layer was extracted with 3×60 ml portions of ethyl acetate. The combined organic extracts were washed with satd NaCl solution and dried over MgSO$_4$. The solids were removed by filtration and the solvent removed in vacuo to give a crude product which was used without further purification.

EXAMPLE 2

Preparation of Ethyl 2-amino-4,7-dihydro-5H-thieno[2,3-c]pyran-3-carboxylate

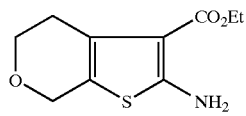

To a mixture of 250 g tetrahydropyran-4-one (0.25 mol) 28.2 g ethyl cyanoacetate (0.25 mol, 26.6 mL) and 18.26 g diethylamine (25.8 mL) in 100 mL ethanol was added 8.4 g sulfur (0.262 mol). A mild exothermic reaction ensured, and the mixture formed a deep red solution. After stirring under argon at room temperature overnight an orange precipitate had formed. The mixture was poured into 200 g of ice and the resulting solid was removed by filtration. The solids

EXAMPLE 3

Preparation of Ethyl 2-Amino-6-[(4-methylphenyl)sulfonyl]-4,5,6,7-tetrahydrothieno [2,3-c]pyridine-3-carboxylate

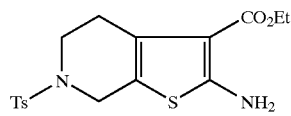

A mixture of 9.21 g ethyl cyanoacetate (0.081 mol), 20.6 g N-tosyl-4-piperidone (0.081 mol), 2.74 g sulfur (0.0855 mol) and 5.95 g diethylamine (0.081 mol, 8.42 mL) in 100 mL ethanol were stirred at rt overnight. The mixture was then filtered to remove some precipitated product and impurities, and the filtrate concentrated in vacuo to give clean product (31.5 g) which was used in subsequent steps without further purification.

EXAMPLE 4

Preparation of 3,5,6,7-Tetrahydro-4H-cyclopenta[4,5]thieno[2,3-d]pyrimidin-4-one

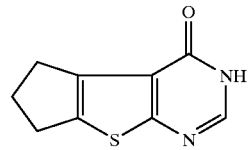

A suspension of 11.37 g ethyl 2-amino-5,6-dihydro-4H-cyclopenta[b]thiophene-3-carboxylate in 40 mL formamide was heated for 4 h to 190° C. using a heating mantle, then cooled and poured into 400 mL water. The mixture was then filtered to remove the solid product. The solids were washed successively with 30 mL EtOAc and 200 mL diethyl ether, air dried overnight, then vacuum oven dried for 3 h. The material was used in the subsequent reactions without further purification.

EXAMPLE 5

Preparation of 5,6,7,8-Tetrahydrol[1]benzothieno[2,3-d]pyrimidin-4 ($^3$H)-one

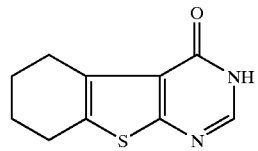

To 68 mL formamide was added 25.0 g (ethyl 2-amino-4,5,6,7-tetrahydro-1-benzo-thiophene-3-carboxylate) and the mixture was heated under argon for 20 h at 180° C., then at 190° C. for 2.5 h. The mixture was cooled to rt, poured into water and then filtered to remove the solid product. The solids were washed successively with water and EtOAc to give 40.7 g of product which was used in the subsequent reactions without further purification.

EXAMPLE 6

Preparation of 4-Chloro-6,7-dihydro-5H-cyclopenta[4,5]thieno[2,3-d]pyrimidine

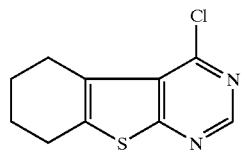

To 10.56 g 5,6,7,8-tetrahydro[1]benzothieno[2,3-d]pyrimidin-4(3H)-one (0.51 mol) and 10 mL dimethylaniline was added, in one portion, 50 mL POCl$_3$. The mixture was heated to reflux for 5 h under argon, cooled and the excess POCl$_3$ was removed by concentration in vacuo. The residue was poured into 200 g ice and neutralized with satd Na$_2$CO$_3$. The resulting blue-gray gum was filtered, washed with water and crystallized from ethanol to give 7.03 g (0.031 mol) of product.

EXAMPLE 7

Preparation of N-(sec-butyl)-5,6,7,8-tetrahydro[1]benzothieno[2,3-d]pyrimidin-4-amine

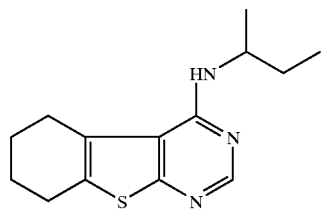

Method A. To 0.250 g 4-chloro-6,7-dihydro-5H-cyclopenta[4,5]thieno[2,3-d]pyrimidine (1.11 mmol) in 12.5 mL t-butanol was added a few drops of 10% HCl solution and 0.203 g (2.38 mmol, 0.28 mL) sec-butylamine. The reaction was refluxed for 16 h. It was then treated with satd NaHCO$_3$ and extracted with EtOAc which was dried and concentrated in vacuo to give white solids. Purification of this crude material by column chromatography, eluting with 20% EtOAc:Hexanes, yielded 0.243 g of pure material, $^1$H NMR:MS 262.1.

Method B. A mixture of 11.1 g of 4-chloro-6,7-dihydro-5H-cyclopenta[4,5]thieno[2,3-d]pyrimidine (0.0494 mol), 15.0 mL sec-butyl amine (0.148 mol), 22.0 mL 1% HCl (aq) and 550 mL water were stirred under argon at reflux for 39 h. The reaction mixture was then cooled, and concentrated in vacuo to 1/10th of its original volume. The concentrate was taken up in EtOAc and washed twice with satd NaHCO$_3$ solution. The organic solution was then dried over MgSO$_4$, filtered and concentrated in vacuo to give 12.7 g of a yellow solid. This material was dissolved in CH$_2$Cl$_2$ and purified using a Biotage® preparative chromatography apparatus, eluting with 5% EtOAc in Hexanes. The mobile phase was gradually increased in polarity, first to 10% EtOAc in Hexanes and then to 15% EtOAc in Hexanes. Fractions were collected and those containing product wee combined and concentrated in vacuo to give 6.60 g pure material.

--- were washed with 2–200 mL portions of water, followed by 100 mL of diethyl ether. A light orange solid remained, weighing 44.6 g (78.6%), TLC (90:1, EtOAc: Hexanes): R$_f$: 0.16.

EXAMPLE 8

Preparation of N,N-diethyl-5,6,7,8-Tetrahydro[1]benzothieno[2,3-d]pyrimidin-4-amine

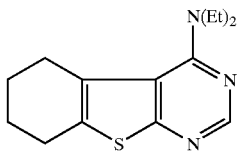

To a slurry of 0.044 g 4-chloro-6,7-dihydro-5H-cyclopenta[4,5]thieno[2,3-d]pyrimidine (0.196 mmol) in 1 mL of 100:1 $H_2O$/HCl was added 0.014 g (0.02 mL, 0.106 mmol) diethylamine. The mixture was heated to reflux, and an additional 0.2 mL diethylamine and 1 mL of t-butanol were added and heated continued at reflux for an additional 1 h. TLC (20% EtOAc/80% pet ether) showed complete reaction and the $^1$H NMR of the isolated material was consistent with the desired product.

EXAMPLE 9

Parallel Synthesis Procedure

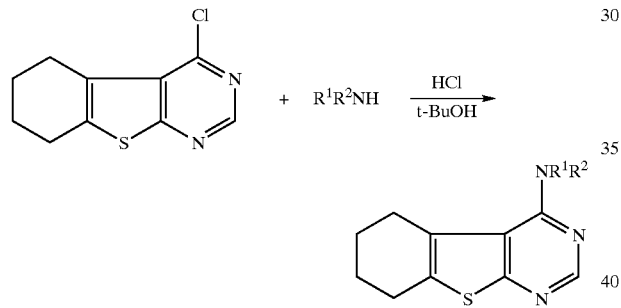

To a vial was containing 1.44 g of (4-chlorothienopyrimidine) in 9.6 mL of 1% HCl(aq) and 38.4 mL of t-butanol was added roughly 1 eq of an amine. The process was repeated for a number of amines, the vials were sealed and placed in a reaction block and heated to 80° C. overnight. After 24 hours the reactions were checked for starting material via TLC (20% EtOAc/80% pet ether). The majority of the reactions showed the presence of starting material. An additional equivalent of amine was added to each reaction and they were again heated overnight. The reactions were then cooled to room temperature and 0.5 mL of sat $NaHCO_3$ was added. The mixtures were filtered through Extrelut® NT in a solid phase extraction column (SPE column) and washed with 7 mL of EtOAc. The reactions were conc in a speed vac, diluted in methanol/DMSO and purified by HPLC and characterized by $^1$H NMR (acetone-$d_6$) and analytical HPLC.

Using a combination of the above exemplified procedures and the appropriate starting materials, compounds which are shown in Tables 1–3 were prepared. Preferred compounds of the invention include Example Nos. 109, 141, 53, 195, 262, 309, 273, 163, 87, 145, and 147.

TABLE 1

| Ex. No. | Formula I compound |
|---|---|
| 10 | |
| 11 | |
| 12 | |
| 13 | |

TABLE 1-continued
| Ex. No. | Formula I compound |
|---|---|
| 14 | 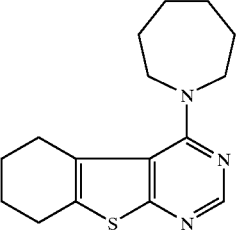 ClH |
| 15 | 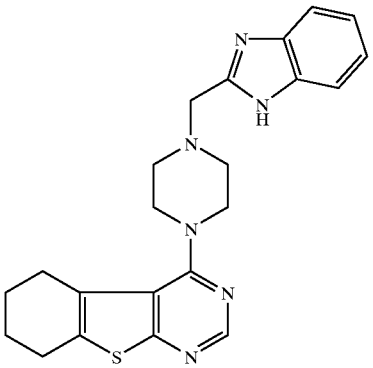 |
| 16 | 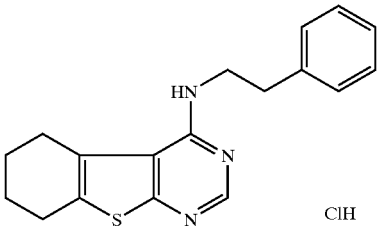 ClH |
| 17 | 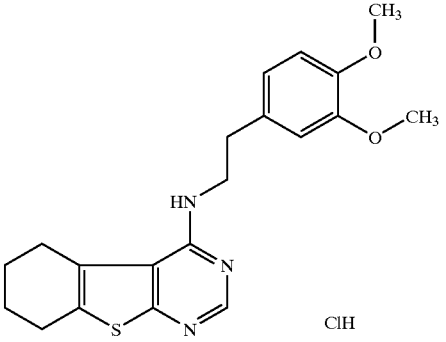 ClH |
| 18 | 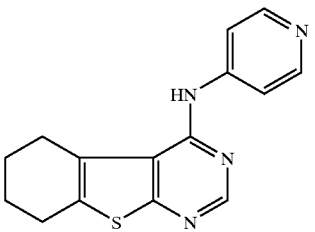 ClH |
| 19 | 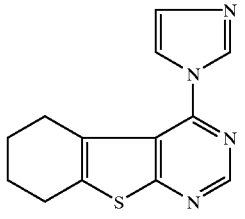 |
| 20 | 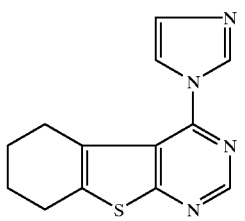 |
| 21 | 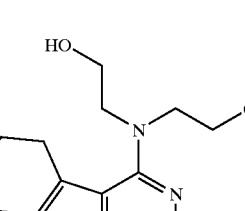 |
| 22 | 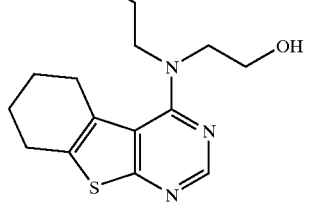 |
| 23 | 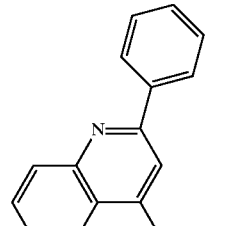 ClH |

TABLE 1-continued
| Ex. No. | Formula I compound |
|---|---|
| 24 | 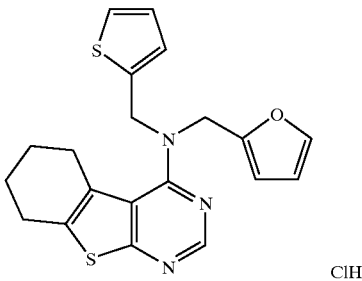 ClH |
| 25 | 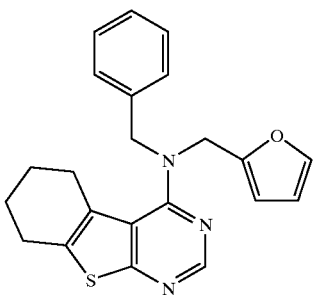 ClH |
| 26 | 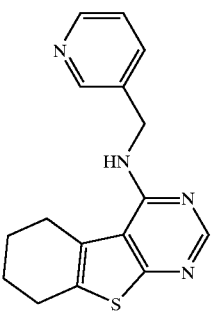 ClH |
| 27 | 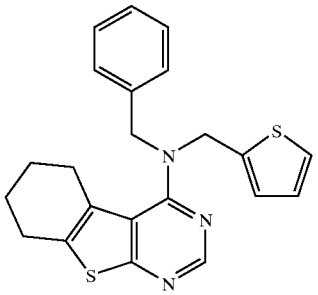 ClH |
TABLE 1-continued
| Ex. No. | Formula I compound |
|---|---|
| 28 | 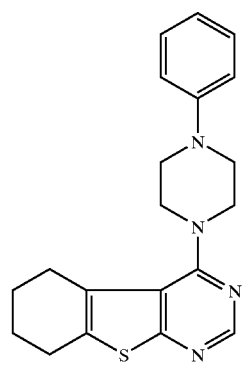 ClH |
| 29 | 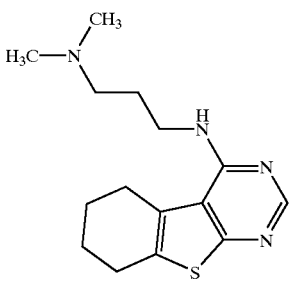 ClH |
| 30 | 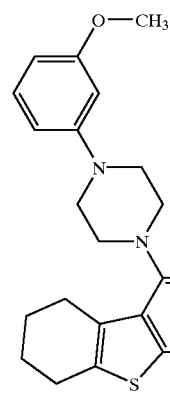 ClH |
| 31 | 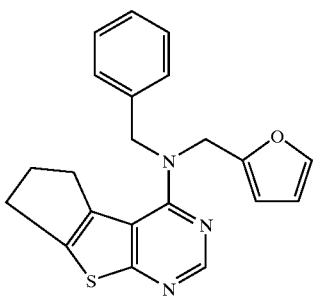 ClH |

TABLE 1-continued
| Ex. No. | Formula I compound |
|---|---|
| 32 | 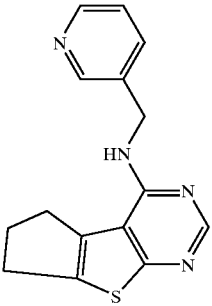 ClH |
| 33 | 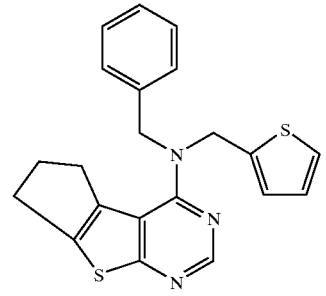 ClH |
| 34 | 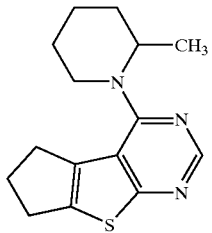 ClH |
| 35 | 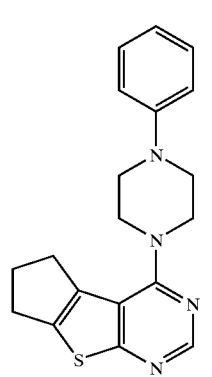 ClH |
| 36 | 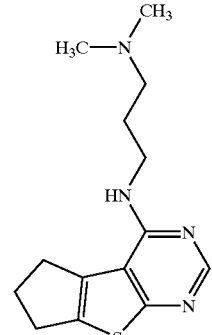 ClH |
| 37 | 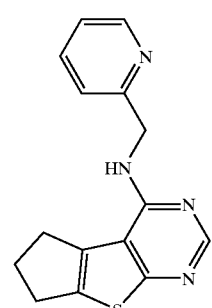 ClH |
| 38 | 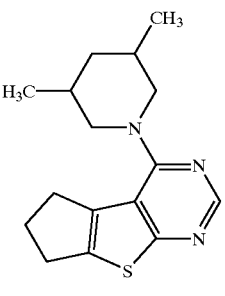 ClH |
| 39 | 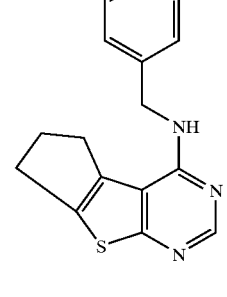 ClH |
| 40 | 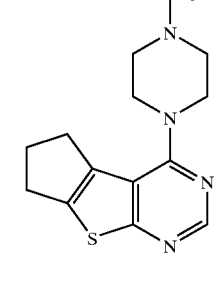 ClH |

TABLE 1-continued

| Ex. No. | Formula I compound |
|---|---|
| 41 | (4-benzylpiperazinyl cyclopenta-thieno-pyrimidine), ClH |
| 42 | (4-(2-pyridyl)piperazinyl cyclopenta-thieno-pyrimidine), ClH · ClH |
| 43 | (furan-2-ylmethylamino cyclopenta-thieno-pyrimidine), ClH |
| 44 | (3,4-dimethoxyphenethylamino cyclopenta-thieno-pyrimidine), ClH |
| 45 | (3,5-dimethylpyrazol-1-yl cyclopenta-thieno-pyrimidine) |
| 46 | (2,4-dibromophenylamino tetrahydrobenzo-thieno-pyrimidine) |
| 47 | (4-chlorophenylamino tetrahydrobenzo-thieno-pyrimidine) |
| 48 | (n-butylamino tetrahydrobenzo-thieno-pyrimidine) |
| 49 | (furan-2-carboxamido tetrahydrobenzo-thieno-pyrimidine) |
| 50 | (2-hydroxyethylamino tetrahydrobenzo-thieno-pyrimidine) |

TABLE 1-continued

| Ex. No. | Formula I compound |
|---------|-------------------|
| 51 | |
| 52 | |
| 53 | |
| 54 | |
| 55 | |
| 56 | |
| 57 | |
| 58 | |
| 59 | |
| 60 | |
| 61 | |
| 62 | |

TABLE 1-continued
| Ex. No. | Formula I compound |
|---|---|
| 63 | 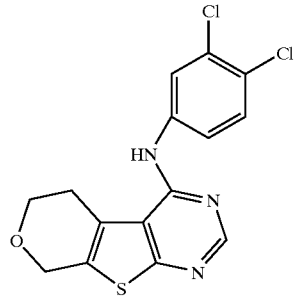 |
| 64 | 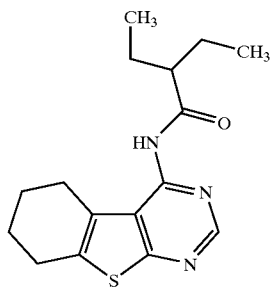 |
| 65 | 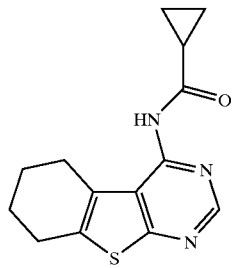 |
| 66 | 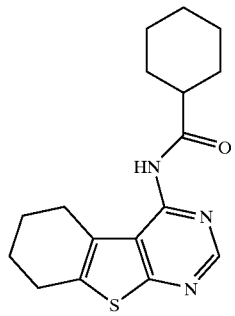 |
| 67 | 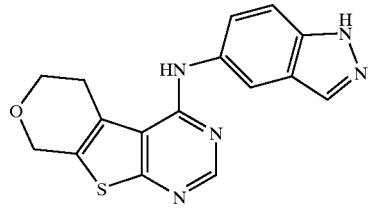 |
| 68 | 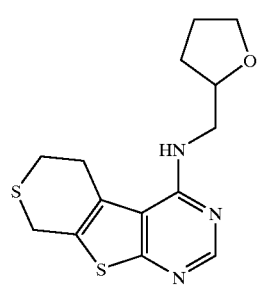 |
| 69 | 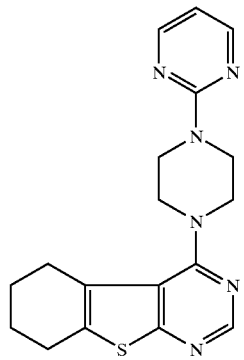 |
| 70 | 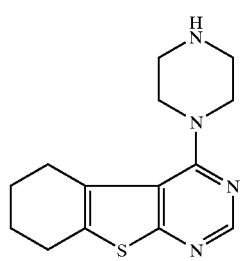 |

TABLE 2

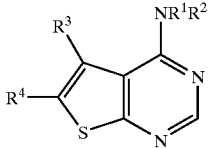

| Ex. No. | R¹ | R₂ | —R₃—R₄— |
|---|---|---|---|
| 71 | Et | Et | —(CH$_2$)$_4$— |
| 72 | Me | 1-naphthyl-CH$_2$— | —(CH$_2$)$_4$— |
| 73 | PhCH$_2$— | PhCH$_2$— | |
| 74 | H | 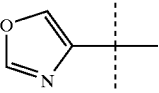 | —(CH$_2$)$_4$— |
| 75 | H | n-Pr | —(CH$_2$)$_4$— |
| 76 | H | MeOCH$_2$CH$_2$— | —(CH$_2$)$_4$— |
| 77 | H | t-Bu | —(CH$_2$)$_4$— |
| 78 | H | cyc-Bu | —(CH$_2$)$_4$— |
| 79 | H | 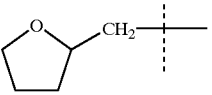 | —(CH$_2$)$_4$— |
| 80 | H | neo-Pent | —(CH$_2$)$_4$— |
| 81 | H | cyc-Hex | —(CH$_2$)$_4$— |
| 82 | H | 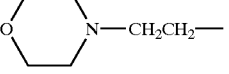 | —(CH$_2$)$_4$— |
| 83 | H | (Me)$_2$CHCH$_2$CH(Me)— | —(CH$_2$)$_4$— |
| 84 | H | 3,4-(Cl)$_2$—Ph— | —(CH$_2$)$_4$— |
| 85 | H | 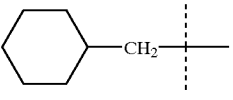 | —(CH$_2$)$_4$— |
| 86 | H | 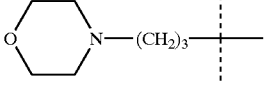 | —(CH$_2$)$_4$— |
| 87 | H | 4-CF$_3$—Ph— | —(CH$_2$)$_4$— |
| 88 | H | 3,4-(Cl)$_2$—PhCH$_2$— | —(CH$_2$)$_4$— |
| 89 | H | 4-Cl—PhCH$_2$CH$_2$— | —(CH$_2$)$_4$— |
| 90 | Et | Ph | —(CH$_2$)$_4$— |
| 91 | i-Bu | i-Bu | —(CH$_2$)$_4$— |
| 92 | H | 2-F-4-CF$_3$—PhCH$_2$— | —(CH$_2$)$_4$— |
| 93 | H | 2-CF$_3$—PhCH$_2$— | —(CH$_2$)$_4$— |
| 94 | H | 3-CF$_3$—PhCH$_2$— | —(CH$_2$)$_4$— |
| 95 | H | 3,5-(MeO)$_2$—PhCH$_2$— | —(CH$_2$)$_4$— |
| 96 | cyc-Hex | i-Pr | —(CH$_2$)$_4$— |
| 97 | H | 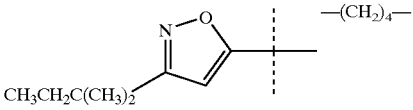 | —(CH$_2$)$_4$— |
| 98 | H | 4-Ph—Ph— | —(CH$_2$)$_4$— |
| 99 | H | CH$_2$=CH—CH$_2$— | —(CH$_2$)$_4$— |
| 100 | H | i-Pr | —(CH$_2$)$_4$— |
| 101 | H | cyc-Pent | —(CH$_2$)$_4$— |
| 102 | i-Pr | i-Pr | —(CH$_2$)$_4$— |
| 103 | H | 4-Me—Ph— | —(CH$_2$)$_4$— |
| 104 | H | 2-Me—Ph— | —(CH$_2$)$_4$— |

TABLE 2-continued
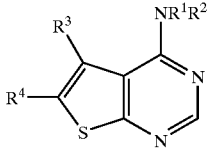
| Ex. No. | R¹ | R₂ | —R₃—R₄— |
|---|---|---|---|
| 105 | H | cyc-Pr | —(CH$_2$)$_4$— |
| 106 | Me | i-Pr | —(CH$_2$)$_4$— |
| 107 | H | (Me)$_2$CHCH(Me)— | —(CH$_2$)$_4$— |
| 108 | H | i-Pr(CO)— | —(CH$_2$)$_4$— |
| 109 | H | (n-Pr)$_2$CH(CO)— | —(CH$_2$)$_4$— |
| 110 | H | Ph(CO)— | —(CH$_2$)$_4$— |
| 111 | Ph(CO)— | Ph(CO)— | —(CH$_2$)$_4$— |
| 112 | H | EtO$_2$C— | —(CH$_2$)$_4$— |
| 113 | H | 2-EtO—PhCH$_2$— | —(CH$_2$)$_4$— |
| 114 | H | PhCH(Et)— | —(CH$_2$)$_4$— |
| 115 | Me | 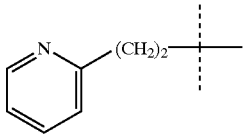 | —(CH$_2$)$_4$— |
| 116 | H | 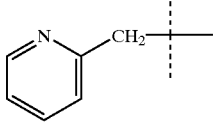 | —(CH$_2$)$_4$— |
| 117 | H | 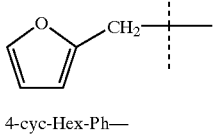 | —(CH$_2$)$_4$— |
| 118 | H | 4-cyc-Hex-Ph— | —(CH$_2$)$_4$— |
| 119 | H | 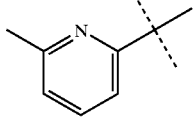 | —(CH$_2$)$_4$— |
| 120 | H | 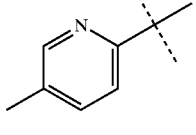 | —(CH$_2$)$_4$— |
| 121 | H | 2-Et—Ph— | —(CH$_2$)$_4$— |
| 122 | H | 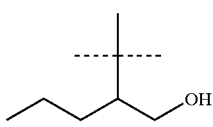 | —(CH$_2$)$_4$— |
| 123 | H | 4-F—Ph— | —(CH$_2$)$_4$— |
| 124 | H | 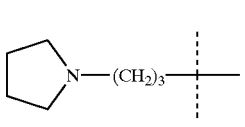 | —(CH$_2$)$_4$— |
| 125 | H | (Me)$_2$NCH$_2$CH$_2$— | —(CH$_2$)$_4$— |

TABLE 2-continued
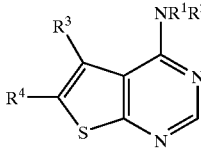
| Ex. No. | R¹ | R₂ | —R₃—R₄— |
|---|---|---|---|
| 126 | H | 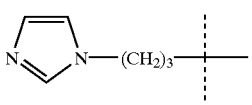 | —(CH₂)₄— |
| 127 | H | 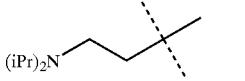 (iPr)₂N | —(CH₂)₄— |
| 128 | H | 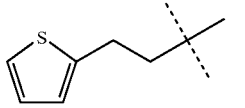 | —(CH₂)₄— |
| 129 | H | 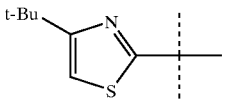 t-Bu | —(CH₂)₄— |
| 130 | H | 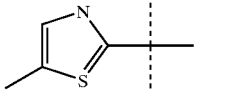 | —(CH₂)₄— |
| 131 | H | 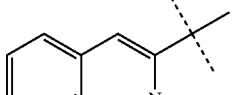 | —(CH₂)₄— |
| 132 | H | 2,3-(Me)₂—Ph— | —(CH₂)₄— |
| 133 | H | Ph | —(CH₂)₄— |
| 134 | H | PhCH₂— | —(CH₂)₄— |
| 135 | H | 4-Et—Ph— | —(CH₂)₄— |
| 136 | H | 2-i-Pr—Ph— | —(CH₂)₄— |
| 137 | H | 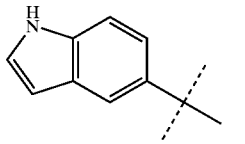 | —(CH₂)₄— |
| 138 | H | 3-F—Ph— | —(CH₂)₄— |
| 139 | H | sec-Bu | —(CH₂)₄— |
| 140 | H | HOCH₂CH₂— | —(CH₂)₄— |
| 141 | H | 4-Me-PhSO₂— | —(CH₂)₄— |
| 142 | H | H | —(CH₂)₄— |
| 143 | H | 3,4-(MeO)₂—PhCH₂— | —(CH₂)₄— |
| 144 | H | H | —(CH₂)₅— |
| 145 | H | n-Pr | —(CH₂)₅— |
| 146 | H | MeOCH₂CH₂— | —(CH₂)₅— |
| 147 | H | cyc-Bu | —(CH₂)₅— |
| 148 | H | cyc-Hex | —(CH₂)₅— |
| 149 | H | cyc-HexCH₂— | —(CH₂)₅— |
| 150 | H | i-Pr | —(CH₂)₅— |
| 151 | i-Pr | i-Pr | —(CH₂)₅— |
| 152 | H | H₂C=CH—CH₂— | —(CH₂)₅— |
| 153 | Et | Et | —(CH₂)₅— |

TABLE 2-continued

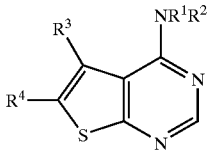

| Ex. No. | R¹ | R₂ | —R₃—R₄— |
|---|---|---|---|
| 154 | H | 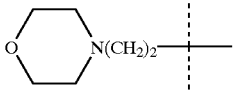 | —(CH₂)₅— |
| 155 | H | sec-Bu | —(CH₂)₅— |
| 156 | H | 3,4-(Cl)₂—Ph— | —(CH₂)₅— |
| 157 | H | 4-CF₃—Ph— | —(CH₂)₅— |
| 158 | H | cyc-Pent | —(CH₂)₅— |
| 159 | H | n-Pr | —(CH₂)₃— |
| 160 | H | MeOCH₂CH₂— | —(CH₂)₃— |
| 161 | H | H₂C=CH—CH₂— | —(CH₂)₃— |
| 162 | Et | Et | —(CH₂)₃— |
| 163 | H | 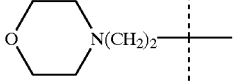 | —(CH₂)₃— |
| 164 | H | sec-Bu | —(CH₂)₃— |
| 165 | H | cyc-Bu | —(CH₂)₃— |
| 166 | H | cyc-Hex | —(CH₂)₃— |
| 167 | H | cyc-HexCH₂— | —(CH₂)₃— |
| 168 | H | i-Pr | —(CH₂)₃— |
| 169 | i-Pr | i-Pr | —(CH₂)₃— |
| 170 | H | 3,4-(Cl)₂—Ph— | —(CH₂)₃— |
| 171 | H | 4-CF₃—Ph— | —(CH₂)₃— |
| 172 | H | cyc-Pent | —(CH₂)₃— |
| 173 | H | Ph | —(CH₂)₃— |
| 174 | H | 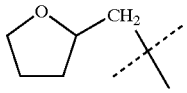 | —(CH₂)₃— |
| 175 | H | (Me)₂CHCH₂CH(Me)— | —(CH₂)₃— |
| 176 | H | 4-Me—Ph— | —(CH₂)₃— |
| 177 | H | 2-Me—Ph— | —(CH₂)₃— |
| 178 | H | 3,4-(MeO)₂—PhCH₂— | —(CH₂)₃— |
| 179 | H | cyc-Bu | —CH₂CH₂CH(Me)CH₂— |
| 180 | Me | n-Pr | —CH₂CH₂CH(Me)CH₂— |
| 181 | Et | Et | —CH₂CH₂CH(Me)CH₂— |
| 182 | i-Bu | H | —CH(Me)(CH₂)₃— |
| 183 | H | cyc-Bu | —CH(Me)(CH₂)₃— |
| 184 | Et | Et | —CH(Me)(CH₂)₃— |
| 185 | H | i-PrCH(Me)— | —(CH₂)₂CH(Me)CH₂— |
| 186 | H | 2-EtO—PhCH₂— | —(CH₂)₂OCH₂— |
| 187 | H | 2-EtO—PhCH₂— | —(CH₂)₂SCH₂— |
| 188 | H | PhCH(Et)— | —(CH₂)₂OCH₂— |
| 189 | H | PhCH(Et)— | —(CH₂)₂SCH₂— |
| 190 | H | 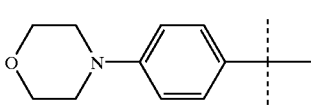 | —(CH₂)₂OCH₂— |
| 191 | H | 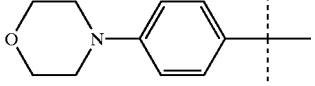 | —(CH₂)₂SCH₂— |

TABLE 2-continued
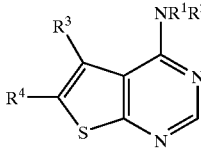
| Ex. No. | R¹ | R₂ | —R₃—R₄— |
|---|---|---|---|
| 192 | H | 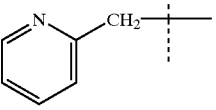 | —(CH$_2$)$_2$OCH$_2$— |
| 193 | H | 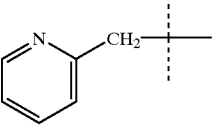 | —(CH$_2$)$_2$SCH$_2$— |
| 194 | Me | 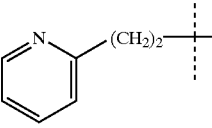 | —(CH$_2$)$_2$OCH$_2$— |
| 195 | Me | 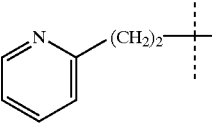 | —(CH$_2$)$_2$SCH$_2$— |
| 196 | H | 2-CF$_3$—PhCH$_2$— | —(CH$_2$)$_2$OCH$_2$— |
| 197 | H | 2-CF$_3$—PhCH$_2$— | —(CH$_2$)$_2$SCH$_2$— |
| 198 | H | cyc-Pr | —(CH$_2$)$_2$OCH$_2$— |
| 199 | H | cyc-Pr | —(CH$_2$)$_2$SCH$_2$— |
| 200 | H | 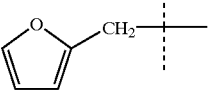 | —(CH$_2$)$_2$OCH$_2$— |
| 201 | H | 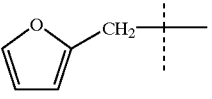 | —(CH$_2$)$_2$SCH$_2$— |
| 202 | H | 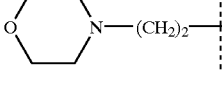 | —(CH$_2$)$_2$OCH$_2$— |
| 203 | H | 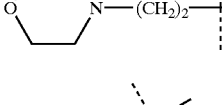 | —(CH$_2$)$_2$SCH$_2$— |
| 204 | H | 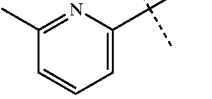 | —(CH$_2$)$_2$OCH$_2$— |

TABLE 2-continued
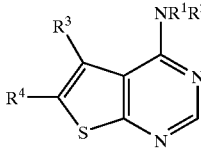
| Ex. No. | R[1] | R[2] | —R[3]—R[4]— |
|---|---|---|---|
| 205 | H | 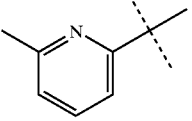 | —(CH$_2$)$_2$SCH$_2$— |
| 206 | H | 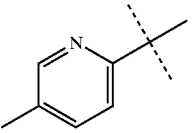 | —(CH$_2$)$_2$OCH$_2$— |
| 207 | H | 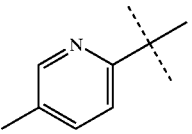 | —(CH$_2$)$_2$SCH$_2$— |
| 208 | H | 2-Et—Ph— | —(CH$_2$)$_2$OCH$_2$— |
| 209 | H | 2-Et—Ph— | —(CH$_2$)$_2$SCH$_2$— |
| 210 | H | 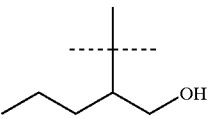 | —(CH$_2$)$_2$OCH$_2$— |
| 211 | H | 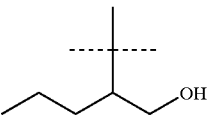 | —(CH$_2$)$_2$SCH$_2$— |
| 212 | H | 4-F—Ph— | —(CH$_2$)$_2$OCH$_2$— |
| 213 | H | 4-F—Ph— | —(CH$_2$)$_2$SCH$_2$— |
| 214 | H | cyc-Pent | —(CH$_2$)$_2$OCH$_2$— |
| 215 | H | cyc-Pent | —(CH$_2$)$_2$SCH$_2$— |
| 216 | H | 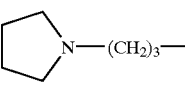 | —(CH$_2$)$_2$OCH$_2$— |
| 217 | H | 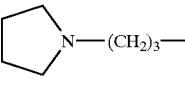 | —(CH$_2$)$_2$SCH$_2$— |
| 218 | H | (Me)$_2$NCH$_2$CH$_2$— | —(CH$_2$)$_2$OCH$_2$— |
| 219 | H | (Me)$_2$NCH$_2$CH$_2$— | —(CH$_2$)$_2$SCH$_2$— |
| 220 | H | 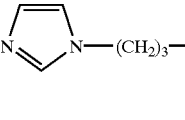 | —(CH$_2$)$_2$OCH$_2$— |
| 221 | H | 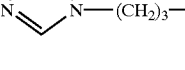 | —(CH$_2$)$_2$SCH$_2$— |

TABLE 2-continued
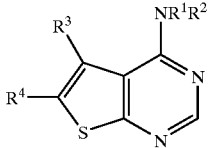
| Ex. No. | R¹ | R₂ | —R₃—R₄— |
|---|---|---|---|
| 222 | H | 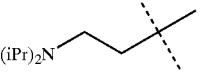(iPr)₂N | —(CH₂)₂OCH₂— |
| 223 | H | 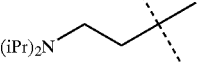(iPr)₂N | —(CH₂)₂SCH₂— |
| 224 | H | 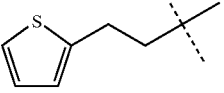 | —(CH₂)₂OCH₂— |
| 225 | H | 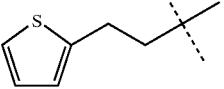 | —(CH₂)₂SCH₂— |
| 226 | H | 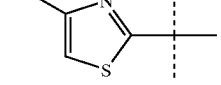t-Bu | —(CH₂)₂OCH₂— |
| 227 | H | 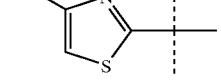t-Bu | —(CH₂)₂SCH₂— |
| 228 | H | 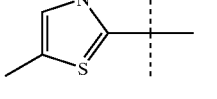 | —(CH₂)₂OCH₂— |
| 229 | H | 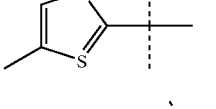 | —(CH₂)₂SCH₂— |
| 230 | H | 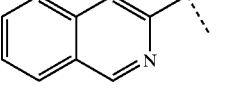 | —(CH₂)₂OCH₂— |
| 231 | H | 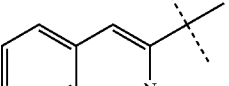 | —(CH₂)₂SCH₂— |
| 232 | H | 2,3-(Me)₂—Ph— | —(CH₂)₂OCH₂— |
| 233 | H | 2,3-(Me)₂—Ph— | —(CH₂)₂SCH₂— |
| 234 | H | Ph | —(CH₂)₂OCH₂— |
| 235 | H | Ph | —(CH₂)₂SCH₂— |
| 236 | H | PhCH₂— | —(CH₂)₂OCH₂— |
| 237 | H | PhCH₂— | —(CH₂)₂SCH₂— |
| 238 | H | 4-Et—Ph— | —(CH₂)₂OCH₂— |
| 239 | H | 4-Et—Ph— | —(CH₂)₂SCH₂— |

TABLE 2-continued

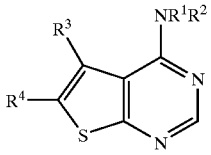

| Ex. No. | R¹ | R₂ | —R₃—R₄— |
|---|---|---|---|
| 240 | H | 2-i-Pr—Ph— | —(CH₂)₂OCH₂— |
| 241 | H | 2-i-Pr—Ph— | —(CH₂)₂SCH₂— |
| 242 | H | 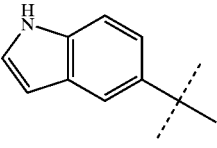 | —(CH₂)₂OCH₂— |
| 243 | H | 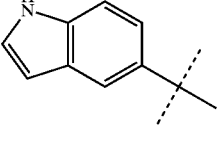 | —(CH₂)₂SCH₂— |
| 244 | H | 3-F—Ph— | —(CH₂)₂OCH₂— |
| 245 | H | 3-F—Ph— | —(CH₂)₂SCH₂— |
| 246 | H | 2-n-Pr—Ph— | —CH₂CH₂SCH₂— |
| 247 | H | 2-sec-Bu—Ph— | —CH₂CH₂SCH₂— |
| 248 | n-Pr | n-Pr | —CH₂CH₂SCH₂— |
| 249 | Et | Et | —CH₂CH₂SCH₂— |
| 250 | H | (Me)₂CHCH(Me)— | —CH₂CH₂N(CH₂Ph)CH₂— |
| 251 | Et | Et | —(CH₂)₂NHCH₂— |
| 252 | H | n-Pr | —(CH₂)₂OCH₂— |
| 253 | H | MeOCH₂CH₂— | —(CH₂)₂OCH₂— |
| 254 | H | cyc-Bu | —(CH₂)₂OCH₂— |
| 255 | H | cyc-Hex | —(CH₂)₂OCH₂— |
| 256 | H | 3,4-(Cl)₂—Ph | —(CH₂)₂OCH₂— |
| 257 | H | sec-Bu | —(CH₂)₂OCH₂— |
| 258 | H | (Me)₂CHCH₂CH(Me)— | —(CH₂)₂OCH₂— |
| 259 | H | 2-Me—Ph— | —(CH₂)₂OCH₂— |
| 260 | H | 4-Me—Ph— | —(CH₂)₂OCH₂— |
| 261 | H | 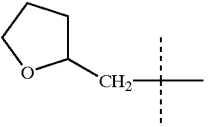 | —(CH₂)₂OCH₂— |
| 262 | H | 4-CF₃—Ph— | —(CH₂)₂OCH₂— |
| 263 | H | (Me)₂CHCH(Me)— | —(CH₂)₂OCH₂— |
| 264 | H | 3,4-(MeO)₂—PhCH₂— | —(CH₂)₂OCH₂— |
| 265 | H | neo-Pent | —(CH₂)₂SCH₂— |
| 266 | H | i-Pr | —(CH₂)₂SCH₂— |
| 267 | H | (Me)₂CHCH₂CH(Me)— | —(CH₂)₂SCH₂— |
| 268 | H | 3-Me—Ph— | —(CH₂)₂SCH₂— |
| 269 | H | 2-Me—Ph— | —(CH₂)₂SCH₂— |
| 270 | H | (Me)₂CHCH(Me)— | —(CH₂)₂SCH₂— |
| 271 | H | EtCH(Me)— | —(CH₂)₂SCH₂— |
| 272 | H | cyc-Bu | —(CH₂)₂SCH₂— |

TABLE 3

[Structure: thieno[2,3-d]pyrimidine with R³ at 5-position, R⁴ at 6-position, NR¹R² at 4-position]

| Ex. No. | R¹ | R² | —R₃—R₄— |
|---|---|---|---|
| 273 | —CH₂CH₂CHCH₂CH₂— (with PhCH₂ branch) | | —(CH₂)₄— |
| 274 | —CH₂CH₂SCH₂— | | —(CH₂)₄— |
| 275 | —CH₂CH(Me)CH₂CH(Me)CH₂— | | —(CH₂)₄— |
| 276 | —CH₂C(Me)₂CH₂CH₂CH₂— | | —(CH₂)₄— |
| 277 | —CH(Me)CH₂CH₂CH₂CH(Me)— | | —(CH₂)₄— |
| 278 | —(CH₂)₄CH(Et)— | | —(CH₂)₄— |
| 279 | —(CH₂)₄CH(Me)— | | —(CH₂)₄— |
| 280 | —CH₂CH(Me)CH₂CH₂CH₂— | | —(CH₂)₄— |
| 281 | —CH(n-Pr)CH₂CH₂CH₂CH₂— | | —(CH₂)₄— |
| 282 | —(CH₂)₄— | | —(CH₂)₄— |
| 283 | —CH₂CH₂SCH₂CH₂— | | —(CH₂)₄— |
| 284 | —(CH₂)₅— | | —(CH₂)₄— |
| 285 | —CH(Me)CH₂CH₂CH₂— | | —(CH₂)₄— |
| 286 | —CH₂CH₂N(Me)CH₂CH₂— | | —(CH₂)₄— |
| 287 | —CH₂CH₂OCH₂CH₂— | | —(CH₂)₄— |
| 288 | —CH₂CH(Me)CH₂CH₂— | | —(CH₂)₄— |
| 289 | —CH₂CH₂CH₂CH(Me)— | | —(CH₂)₃— |
| 290 | —CH₂CH₂OCH₂CH₂— | | —(CH₂)₃— |
| 291 | —CH₂CH₂SCH₂— | | —(CH₂)₃— |
| 292 | —CH₂CH₂SCH₂CH₂— | | —(CH₂)₃— |
| 293 | —(CH₂)₆— | | —(CH₂)₃— |
| 294 | —CH₂CH₂CH(Me)CH₂CH₂— | | —(CH₂)₃— |
| 295 | —CH₂CH₂CH₂CH₂— | | —CH₂CH₂—CH(CH₃)—CH₂— |
| 296 | —(CH₂)₄— | | —(CH₂)₂OCH₂— |
| 297 | —(CH₂)₅— | | —(CH₂)₂OCH₂— |
| 298 | —(CH₂)₃CH(CH₂OH)CH₂— | | —(CH₂)₄— |
| 299 | —(CH₂)₃CH(Me)— | | —(CH₂)₂OCH₂— |
| 300 | —(CH₂)₆— | | —(CH₂)₂OCH₂— |
| 301 | —(CH₂)₂SCH₂— | | —(CH₂)₂OCH₂— |
| 302 | —(CH₂)₃C(Me)₂CH₂— | | —(CH₂)₂OCH₂— |
| 303 | —(CH₂)₄CH(Me)— | | —(CH₂)₂OCH₂— |
| 304 | —(CH₂)₂O(CH₂)₂— | | —(CH₂)₂OCH₂— |
| 305 | —(CH₂)₄CH(Et)— | | —(CH₂)₂OCH₂— |
| 306 | —CH₂CH(Me)CH₂CH(Me)CH₂— | | —(CH₂)₂OCH₂— |
| 307 | —CH(Me)(CH₂)₃CH(Me)— | | —(CH₂)₂OCH₂— |
| 308 | —(CH₂)₂CH(Me)(CH₂)₂— | | —(CH₂)₂OCH₂— |
| 309 | —(CH₂)₂—N(3-CF₃—Ph)—(CH₂)₂— | | —(CH₂)₂OCH₂— |
| 310 | —(CH₂)₄— | | —(CH₂)₂SCH₂— |
| 311 | —(CH₂)₅— | | —(CH₂)₂SCH₂— |
| 312 | —CH=CH—C(CF₃)=N— | | —(CH₂)₂SCH₂— |
| 313 | —(CH₂)₆— | | —(CH₂)₂SCH₂— |
| 314 | —(CH₂)₄— | | —(CH₂)₅— |
| 315 | —(CH₂)₅— | | —(CH₂)₅— |
| 316 | —(CH₂)₂O(CH₂)₂— | | —(CH₂)₂SCH₂— |
| 317 | —(CH₂)₃CH(Me)CH₂— | | —(CH₂)₂SCH₂— |
| 318 | —(CH₂)₃CH(Me)CH₂— | | —(CH₂)₂OCH₂— |
| 319 | —(CH₂)₂S(CH₂)₂— | | —(CH₂)₅— |
| 320 | —(CH₂)₄CH(Et)— | | —(CH₂)₂SCH₂— |
| 321 | —(CH₂)₅— | | —(CH₂)₃— |
| 322 | —(CH₂)₄— | | —(CH₂)₃— |

Screening Assay

To determine whether a compound is able to modulate $PDE7_B$ activity, the following procedure was used.

Materials:
SPA 96 well Isoplates (Wallac 1450–515)
Phosphodiesterase scintillation proximity (SPA) beads (Amersham RPNQ 0150)
$^3$H cAMP tracer (Amersham TRK 559–250 µCi)
PDE7b enzyme (See procedure)
Assay buffer (50 mM Tris/HCl pH 7.5, 8.3 mM $MgCl_2$, 1.7 mM EGTA)

Method:

SPA beads were prepared according to manufacturer's directions. $H_2O$ (28 ml) was added to 500 mg vial. Radio-labeled camp tracer was prepared ($^3$H cAMP tracer stock vial is 1 µCi/µl) 1:400 in Assay buffer. A dilution of PDE7b enzyme (1:800 dilution) was prepared and placed on ice in cold Assay buffer. Assay buffer was added to all wells of a microtiter plate. Wells of only background buffer and of enzyme were prepared for controls. Compounds to be assayed were added to wells, followed by enzyme addition. The enzyme reaction was started by addition of $^3$H cAMP tracer to each well. Wells were incubated at room temperature for 45 minutes. The reaction was stopped with the addition of SPA beads to each well. Scintillation measurements were taken after plates were sealed and at least one hour had passed. All of the compounds reported as Example Numbers 7–322 showed ability to modulate enzyme activity.

Tissue Assay

The inhibition of $PDE7_B$ in tissue culture cells was measured using a kit supplied by Amersham Corp., cAMP EIA, #RPN225. Compounds reported in the Examples showed ability to inhibit cAMP degradation by $PDE7_B$.

The invention may be embodied in other specific forms without departing from the spirit or essential characteristics thereof. The foregoing examples are included by way of illustration only. Accordingly, the scope of the invention is limited only by the scope of the appended claims.

What is claimed is:

1. A compound according to formula I:

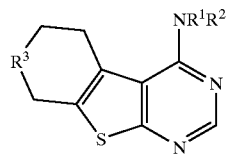

wherein $R^1$ and $R^2$ are independently selected from the group consisting of
hydrogen,
alkyl of 1–8 carbon atoms,
alkenyl of 2–8 carbon atoms,
alkynyl of 2–8 carbon atoms,
cycloalkyl of 3–7 carbon atoms,
fully saturated heterocycle of 2–6 carbon atoms and 1–2 heteroatoms selected from NH, S and O,
aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O,
heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O, and $R^4$–$R^5$, or $R^1$ and $R^2$ combine to form, together with the nitrogen atom to which they are attached, a 5–7 membered saturated ring which may contain 1–2 additional heteroatoms selected from the group consisting of NH, $NR^8$, S and O, or combine to form, together with the nitrogen atom to which they are attached, a 5–7 membered unsaturated ring which may contain 1–2 additional heteroatoms selected from the group consisting of N, S and O, wherein said saturated or unsaturated ring may be substituted with 1–2 substituents selected from the group consisting of OH, alkyl of 1–6 carbon atoms, alkenyl of 2–6 carbon atoms, alkynyl of 2–6 carbon atoms, cycloalkyl of 3–7 carbon atoms, fully saturated heterocycle of 2–6 carbon atoms and 1–2 heteroatoms selected from NH, S and O, halogen, haloalkyl of 1–2 carbon atoms and a number of halogen atoms up to the perhalo level, alkoxy of 1–6 carbon atoms, haloalkoxy of 1–6 carbon atoms and a number of halogen atoms up to the perhalo level, and $R^9$–$R^{10}$;

or $R^1$ and $R^2$ combine to form, together with the nitrogen atom to which they are attached, an 8–10 membered bicyclic saturated ring;

$R^3$ is selected from the group consisting of NH, S, $S(=O)_2$, and O;

with the proviso that $R^3$ is not NH when both $R^1$ and $R^2$ are methyl;

with the further proviso that $R^1$ is not butyl, phenyl, or benzyl when $R^2$ is hydrogen and $R^3$ is S or O;

$R^4$ is selected from
alkyl of 1–8 carbon atoms,
alkenyl of 2–8 carbon atoms,
alkynyl of 2–8 carbon atoms,
C(=C),
$S(=O)_2$, and
C(=O)O—;

$R^5$ is selected from
hydrogen,
OH,
alkyl of 1–8 carbon atoms,
alkenyl of 2–8 carbon atom,
alkynyl of 2–8 carbon atoms,
alkoxy of 1–8 carbon atoms,
aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkyl of 1–6 carbon atoms and a number of halogen atoms up to the perhalo level, aryl of 6–12 carbon atoms and heteroaryl of 4–11 carbon atoms and 1–2 heteroatoms selected from N, S and O, heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms and heteroaryl of 4–11 carbon atoms and 1–2 heteroatoms selected from N, S and O, cycloalkyl of 3–7 carbon atoms, fully saturated heterocycle of 2–6 carbon atoms and 1–2 heteroatoms selected from NH, S and O, and $N-R^6-R^7$, with the proviso that $R^5$ is not OH, alkoxy or $N-R^6-R^7$ when $R^4$ is $C(=O)O-$, and with the further proviso that $R^5$ is not alkyl when $R^4$ is alkyl, alkenyl or alkynyl;

$R^6$ and $R^7$ are independently selected from hydrogen, alkyl of 1–8 carbon atoms, alkenyl of 2–8 carbon atoms, and alkynyl of 2–8 carbon atoms, or $R^6$ and $R^7$ combine together with the nitrogen atom to which they are attached to form a 5–7 membered, unsaturated ring which may contain 1–2 additional heteroatoms selected from N, S and O or to form a 5–7 membered, saturated ring which may contain 1–2 additional heteroatoms selected from NH, S and O;

$R^8$ is selected from alkyl of 1–8 carbon atoms, alkenyl of 2–8 carbon atoms, alkynyl of 2–8 carbon atoms, $R^{11}-R^{12}$, cycloalkyl of 3–7 carbon atoms, fully saturated heterocycle of 2–6 carbon atoms and 1–2 heteroatoms selected from NH, S and O, aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O, heteroaryl of 4–11 carbon atoms and 1–2heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O;

$R^9$ is selected from alkyl of 1–8 carbon atoms, alkenyl of 2–8 carbon atoms, and alkynyl of 2–8 carbon atoms, $R^{10}$ is selected from

OH, aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O, and heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O;

$R^{11}$ is selected from alkyl of 1–8 carbon atoms, alkenyl of 2–8 carbon atoms, and alkynyl of 2–8 carbon atoms; and $R^{12}$ is selected from cycloalkyl of 3–7 carbon atoms, fully saturated heterocycle of 2–6 carbon atoms and 1–2 heteroatoms selected from NH, S and O, aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O, and heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O;

and pharmaceutically acceptable salts thereof.

2. The compound of claim 1, wherein $R^3$ is $S(=O)_2$; and $R^4$ is selected from alkyl of 1–8 carbon atoms, alkenyl of 2–8 carbon atoms, alkynyl 2–8 carbon atoms, $C(=O)_2$, and $S(=O)$.

3. A pharmaceutical composition comprising the compound of claim 1 and a pharmaceutically acceptable carrier.

4. A compound according to formula II:

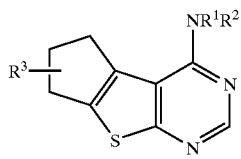

(II)

wherein $R^1$ and $R^2$ are independently selected from the group consisting of
hydrogen,
alkyl of 1–8 carbon atoms,
alkenyl of 2–8 carbon atoms,
alkynyl of 2–8 carbon atoms,
cycloalkyl of 3–7 carbon atoms,
fully saturated heterocycle of 2–6 carbon atoms and 1–2 heteroatoms selected from NH, S and O,
aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O,
heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O, and $R^4$–$R^5$, or $R^1$ and $R^2$ combine to form, together with the nitrogen atom to which they are attached, a 5–7 membered saturated ring which may contain 1–2 additional heteroatoms selected from the group consisting of NH, $NR^8$, S and O, or combine to form, together with the nitrogen atom to which they are attached, a 5–7 membered unsaturated ring which may contain 1–2 additional heteroatoms selected from the group consisting of N, S and O,
wherein said saturated or unsaturated ring may be substituted with 1–2 substituents selected from the group consisting of OH, alkyl of 1–6 carbon atoms, alkenyl of 2–6 carbon atoms, alkynyl of 2–6 carbon atoms, cycloalkyl of 3–7 carbon atoms, fully saturated heterocycle of 2–6 carbon atoms and 1–2 heteroatoms selected from NH, S and O, halogen, haloalkyl of 1–2 carbon atoms and a number of halogen atoms up to the perhalo level, alkoxy of 1–6 carbon atoms, haloalkoxy of 1–6 carbon atoms and a number of halogen atoms up to the perhalo level, and $R^9$–$R^{10}$;

$R^3$ is selected from the group consisting of:
hydrogen,
alkyl of 1–8 carbon atoms,
alkenyl of 2–8 carbon atoms,
alkynyl of 2–8 carbon atoms,
cycloalkyl of 3–7 carbon atoms,
fully saturated heterocycle of 2–6 carbon atoms and 1–2 heteroatoms selected from NH, S and O,
aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O,
heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O, and $R^4$–$R^5$;

$R^4$ is selected from
alkyl of 1–8 carbon atoms,
alkenyl of 2–8 carbon atoms,
alkynyl 2–8 carbon atoms,
C(=O),
S(=O)$_2$, and
C(=O)O—;

$R^5$ is selected from
hydrogen,
OH,
alkyl of 1–8 carbon atoms,
alkenyl 2–8 carbon atoms,
alkynyl 2–8 carbon atoms,
alkoxy of 1–8 carbon atoms,
aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms and heteroaryl of 4–11 carbon atoms and 1–2 heteroatoms selected from N, S and O,
heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms and heteroaryl of 4–11 carbon atoms and 1–2 heteroatoms selected from N, S and O, cycloalkyl of 3–7 carbon atoms,
fully saturated heterocycle of 2–6 carbon atoms and 1–2 heteroatoms selected from NH, S and O, and
N—$R^6$–$R^7$,
with the proviso that $R^5$ is not OH, alkoxy or N—$R^6$–$R^7$ when $R^4$ C(=O)O—, and with the further proviso that $R^5$ is not alkyl when $R^4$ is alkyl, alkenyl or alkynyl;

$R^6$ and $R^7$ are independently selected from
   hydrogen,
   alkyl of 1–8 carbon atoms,
   alkenyl of 2–4 carbon atoms, and
   alkynyl of 2–8 carbon atoms,
or $R^6$ and $R^7$ combine together with the nitrogen atom to which they are attached to form a 5–7 membered, unsaturated ring which may contain 1–2 additional heteroatoms selected from N, S and O or to form a 5–7 membered, saturated ring which may contain 1–2 additional heteroatoms selected from NH, $NR^{11}$, S and O;

$R^8$ is selected from
   alkyl of 1–8 carbon atoms,
   alkenyl of 2–8 carbon atoms,
   alkynyl of 2–8 carbon atoms,
   $R^{12}$–$R^{13}$,
   cycloalkyl of 3–7 carbon atoms,
   fully saturated heterocycle of 2–6 carbon atoms and 1–2 heteroatoms selected from NH, S and O,
   aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O,
   heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O;

$R^9$ is selected from
   alkyl of 1–8 carbon atoms,
   alkenyl of 2–8 carbon atoms, and
   alkynyl of 2–8 carbon atoms;

$R^{10}$ is selected from
   OH,
   aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O and
   heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O;

$R^{11}$ is benzyl which may be substituted with
   alkyl of 1–6 carbon atoms,
   alkenyl of 2–6 carbon atoms,
   alkynyl of 2–6 carbon atoms,
   halogen, and
   $R^{14}$–$R^{15}$;

$R^{12}$ is selected from
   alkyl of 1–8 carbon atoms,
   alkenyl of 2–8 carbon atoms, and
   alkynyl of 2–8 carbon atoms;

$R^{13}$ is selected from
   cycloalkyl of 3–7 carbon atoms,
   fully saturated heterocycle of 2–6 carbon stunts and 1–2 heteroatoms selected from NH, S and O,
   aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a member of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O, and
   heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O;

$R^{14}$ is alkyl of 1–3 carbon atoms;

$R^{15}$ is cycloalkyl of 3–7 carbon atoms;

with the proviso that when $R^3$ is hydrogen, $R^1$ and $R^2$ are independently selected from the group consisting of
   hydrogen, with the further proviso that $R^1$ and $R^2$ are not both hydrogen,
   alkyl of 1–8 carbon atoms, with the further proviso that $R^1$ and $R^2$ are not both ethyl,
   alkenyl of 2–8 carbon atoms,
   alkynyl of 2–8 carbon atoms,
   fully saturated heterocycle of 4–6 carbon atoms and 1–2 heteroatoms selected from NH, S and O, and
   bornyl,
or $R^1$ and $R^2$ combine to form, together with the nitrogen atom to which they are attached,
   an 8–10 membered bicyclic saturated ring;

and pharmaceutically acceptable salts thereof.

5. The compound of claim 4, wherein $R^4$ is selected from
   alkyl of 1–8 carbon atoms,
   alkenyl of 2–8 carbon atoms,
   alkynyl 2–8 carbon atoms,
   C(=O), and
   S(=O)$_2$;

with the proviso that when $R^3$ is hydrogen, $R^1$ and $R^2$ are independently selected from the group consisting of
   hydrogen, with the further proviso that $R^1$ and $R^2$ are not both hydrogen, alkyl of 3–8 carbon atoms,
alkenyl of 2–8 carbon atoms,
alkynyl of 2–8 carbon atoms,
fully saturated heterocycle of 4–6 carbon atoms and 1–2 heteroatoms selected from NH, S and O, and bornyl,
or $R^1$ and $R^2$ combine to form, together with the nitrogen atom to which they are attached, an 8–10 membered bicyclic saturated ring.

6. A pharmaceutical composition comprising the compound of claim 4 and a pharmaceutically acceptable carrier.

7. A compound according to formula III:

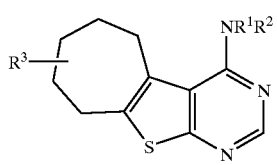

(III)

wherein
$R^1$ and $R^2$ are independently selected from the group consisting of
hydrogen,
alkyl of 1–8 carbon atoms,
alkenyl of 2–8 carbon atoms,
alkynyl of 2–8 carbon atoms,
alkoxy of 1–8 carbon atoms,
cycloalkyl of 3–7 carbon atoms, fully saturated heterocycle of 2–6 carbon atoms and 1–2 heteroatoms selected from NH, S and O,
aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O,
heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O, and $R^4$–$R^5$,
or $R^1$ and $R^2$ combine to form, together with the nitrogen atom to which they are attached, a 5–7 membered saturated ring which may contain 1–2 additional heteroatoms selected from the group consisting of NH, $NR^8$, S and O, or combine to form, together with the nitrogen atom to which they are attached, a 5–7 membered unsaturated ring which may contain 1–2 additional heteroatoms selected from the group consisting of N, S and O,
wherein said saturated or unsaturated ring may be substituted with 1–2 substituents selected from the group consisting of OH, alkyl of 1–6 carbon atoms, alkenyl of 2–6 carbon atoms, alkynyl of 2–6 carbon atoms, cycloalkyl of 3–7 carbon atoms, fully saturated heterocycle of 2–6 carbon atoms and 1–2 heteroatoms selected from NH, S and O, halogen, haloalkyl of 1–2 carbon atoms and a number of halogen atoms up to the perhalo level, alkoxy of 1–6 carbon atoms, haloalkoxy of 1–6 carbon atoms and a number of halogen atoms up to the perhalo level, and $R^9$–$R^{10}$;

$R^3$ is selected from the group consisting of:
hydrogen,
alkyl of 1–8 carbon atoms,
alkenyl of 2–8 carbon atoms,
alkynyl of 2–8 carbon atoms,
cycloalkyl of 3–7 carbon atoms,
fully saturated heterocycle of 2–6 carbon atoms and 1–2 heteroatoms selected from NH, S and O,
aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O,
heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O, and $R^4$–$R^5$, $R^4$ is selected from
alkyl of 1–8 carbon atoms,
alkenyl of 2–8 carbon atoms,
alkynyl of 2–8 carbon atoms,
C(=O),
S(=O)$_2$, and
C(=O)O—;

$R^5$ is selected from
hydrogen,
OH,
alkyl of 1–8 carbon atoms,
alkenyl 2–8 carbon atoms,
alkynyl 2–8 carbon atoms,
alkoxy of 1–8 carbon atoms,
aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms and heteroaryl of 4–11 carbon atoms and 1–2 heteroatoms selected from N, S and O,
heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms and heteroaryl of 4–11 carbon atoms and 1–2 heteroatoms selected from N, S and O, cycloalkyl of 3–7 carbon atoms,
fully saturated heterocycle of 2–6 carbon atoms and 1–2 heteroatoms selected from NH, S and O, and N—$R^6$–$R^7$,
with the proviso that $R^5$ is not OH, alkoxy or N—$R^6$–$R^1$ when $R^4$ is C(=O)O—, and with the further proviso that $R^5$ is not alkyl when $R^4$ is alkyl, alkenyl or alkynyl;

$R^6$ and $R^7$ are independently selected from
hydrogen,
alkyl of 1–8 carbon atoms,
alkenyl of 2–8 carbon atoms, and
alkynyl of 2–8 carbon atoms,
or $R^6$ and $R^7$ combine together with the nitrogen atom to which they are attached to form a 5–7 membered, unsaturated ring which may contain 1–2 additional heteroatoms selected from N, S and O or to form a 5–7 membered, saturated ring which may contain 1–2 additional heteroatoms selected from NH, $NR^{11}$, S and O;

$R^8$ is selected from
alkyl of 1–8 carbon atoms,
alkenyl of 2–8 carbon atoms,
alkynyl of 2–8 carbon atoms,
$R^{12}$–$R^{13}$,
cycloalkyl of 3–7 carbon atoms,
fully saturated heterocycle of 2–6 carbon atoms and 1–2 heteroatoms selected from NH, S and O,
aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O,
heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O;

$R^9$ is selected from
alkyl of 1–8 carbon atoms,
alkenyl of 2–8 carbon atoms, and
alkynyl of 2–8 carbon atoms;

$R^{10}$ is selected from
OH,
aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O, and
heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O;

$R^{11}$ is benzyl which may be substituted with
alkyl of 1–6 carbon atoms,
alkenyl of 2–6 carbon atom;
alkynyl of 2–6 carbon atoms,
halogen, and
$R^{14}$–$R^{15}$;

$R^{12}$ is selected from
alkyl of 1–8 carbon atoms,
alkenyl of 2–8 carbon atoms, and
alkynyl of 2–8 carbon atoms;

$R^{13}$ is selected from
cycloalkyl of 3–7 carbon atoms,
fully saturated heterocycle of 2–6 carbon atoms and 1–2 heteroatoms selected from NH, S and O,
aryl of 6–12 carbon atoms, which may be substituted with alkyl of 1–6 carbon atoms, alkenyl of 2–6 carbon atoms, alkynyl 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O, and
heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O;

$R^{14}$ is alkyl of 1–3 carbon atoms;
$R^{15}$ is cycloalkyl of 3–7 carbon atoms;
with the proviso that when $R^3$ is hydrogen,
$R^1$ and $R^2$ are independently selected from the group consisting of
hydrogen, with the further proviso that only one of $R^1$ and $R^2$ may be hydrogen,
alkyl of 1–8 carbon atoms,
alkenyl of 2–8 carbon atoms,
alkynyl of 2–8 carbon atoms,
alkoxy of 1–8 carbon atoms,
cycloalkyl of 3–7 carbon atoms,
phenyl which may be substituted from one to five times with bromine, chlorine, $CH_3$, $CF_3$, and
$R^4$–$R^5$, with the further proviso that if $R^4$ is methyl then $R^5$ may not be a five membered ring that contains oxygen as one member of the ring and that if $R^4$ is ethyl then $R^5$ may not be substituted or unsubstituted phenyl, or R$^1$ and R$^3$ combine to form, together with the nitrogen atom to which they are attached, a 6–7 membered saturated ring which may contain 1–2 additional heteroatoms selected from the group consisting of NH, NR$^8$, S, and O, or combine to form, together with the nitrogen atom to which they are attached, a 6–7 membered unsaturated ring which may contain 1–2 additional heteroatoms selected from the group consisting of N, S and O, wherein said saturated or unsaturated ring may be substituted with 1–2 substituents selected from the group consisting of OH, alkyl of 1–6 carbon atoms, alkenyl of 2–6 carbon atoms, alkynyl of 2–6 carbon atoms, cycloalkyl of 3–7 carbon atoms, fully saturated heterocycle of 2–6 carbon atoms and 1–2 heteroatoms selected from NH, S and O, halogen, haloalkyl of 1–2 carbon atoms and a number of halogen atoms up to the perhalo level, alkoxy of 1–6 carbon atoms, haloalkoxy of 1–6 carbon atoms and a number of halogen atoms up to the perhalo level, and R$^9$–R$^{10}$;

and pharmaceutically acceptable salts thereof.

8. The compound of claim 7 wherein

R$^4$ is selected from alkyl of 1–8 carbon atoms,
alkenyl of 2–8 carbon atoms,
alkynyl of 2–8 carbon atoms,
C(=O), and
S(=O)$_2$;

with the proviso that when R$^3$ is hydrogen,

R$^1$ and R$^2$ are independently selected from the group consisting of hydrogen, with the further proviso that only one of R$^1$ and R$^2$ may be hydrogen,
alkyl of 1–8 carbon atoms,
alkenyl of 2–8 carbon atoms,
alkynyl of 2–8 carbon atoms,
alkoxy of 1–8 carbon atoms,
cycloalkyl of 3–7 carbon atoms, and
phenyl which may be substituted from one to five times with bromine, chlorine, CH$_3$, or CF$_3$;

or

R$^1$ and R$^2$ combine to form, together with the nitrogen atom to which they are attached, a 6–7 membered saturated ring which may contain 1–2 additional heteroatoms selected from the group consisting of NH, NR$^8$, S, and O, or combine to form, together with the nitrogen atom to which they are attached, a 6–7 membered unsaturated ring which may contain 1–2 additional heteroatoms selected from the group consisting of N, S and O, wherein said saturated or unsaturated ring may be substituted with 1–2 substituents selected from the group consisting of OH, alkyl of 1–6 carbon atoms, alkenyl of 2–6 carbon atoms, alkynyl of 2–6 carbon atoms, cycloalkyl of 3–7 carbon atoms, fully saturated heterocycle of 2–6 carbon atoms and 1–2 heteroatoms selected from NH, S and O, halogen, haloalkyl of 1–2 carbon atoms and a number of halogen atoms up to the perhalo level, alkoxy of 1–6 carbon atoms, haloalkoxy of 1–6 carbon atoms and a number of halogen atoms up to the perhalo level, and R$^9$–R$^{10}$.

9. A pharmaceutical composition comprising the compound of claim 7 and a pharmaceutically acceptable carrier.

10. A compound according to the formula IV:

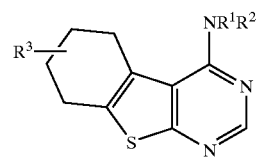

(IV)

wherein

R$^1$ and R$^2$ are independently selected from the group consisting of hydrogen,
alkyl of 1–8 carbon atoms,
alkenyl of 2–8 carbon atoms,
alkynyl of 2–8 carbon atoms,
cycloalkyl of 3–7 carbon atoms,
fully saturated heterocycle of 2–6 carbon atoms and 1–2 heteroatoms selected from NH, S and O,
aryl of 6–12 carbon atoms which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O,
heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O, and R$^4$–R$^5$, or R$^1$ and combine to form, together with the nitrogen atom to which they are attached, a 5–7 membered saturated ring which may contain 1–2 additional heteroatoms selected from the group consisting of NH, NR$^8$, S and O, or combine to form, together with the nitrogen atom to which they are attached, a 5–7 membered unsaturated ring which may contain 1–2 additional heteroatoms selected from the group consisting of N, S and O, wherein said saturated or unsaturated ring may be substituted with 1–2 substituents selected from the group consisting of OH, alkyl of 1–6 carbon atoms, alkenyl of 2–6 carbon atoms, alkynyl of 2–6 carbon atoms, cycloalkyl of 3–7 carbon atoms, fully saturated heterocycle of 2–6 carbon atoms and 1–2 heteroatoms selected from NH, S and O, halogen, haloalkyl of 1–2 carbon atoms and a number of halogen atoms up to the perhalo level, alkoxy of 1–6 carbon atoms, haloalkoxy of 1–6 carbon atoms and a number of halogen atoms up to the perhalo level, and R$^9$–R$^{10}$;

R$^3$ is selected from the group consisting of:

hydrogen,
alkyl of 1–8 carbon atoms,
alkenyl of 2–8 carbon atoms, alkynyl of 2–8 carbon atoms,
cycloalkyl of 3–7 carbon atoms,
fully saturated heterocycle of 2–6 carbon atoms and 1–2 heteroatoms selected from NH, S and O,
aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O,
heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O, and $R^4$–$R^5$, $R^4$ is selected from
alkyl of 1–8 carbon atoms,
alkenyl of 2–8 carbon atoms,
alkynyl 2–8 carbon atoms,
C(=O),
S(=O)$_2$, and
C(=O)O—;

$R^5$ is selected from
hydrogen,
OH,
alkyl of 1–8 carbon atoms,
alkenyl 2–8 carbon atoms,
alkynyl 2–8 carbon atoms,
alkoxy of 1–8 carbon atoms,
aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms and heteroaryl of 4–11 carbon atoms and 1–2 heteroatoms selected from N, S and O,
heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms and heteroaryl of 4–11 carbon atoms and 1–2 heteroatoms selected from N, S and O, cycloalkyl of 3–7 carbon atoms,
fully saturated heterocycle of 2–6 carbon atoms and 1–2 heteroatoms selected from NH, S and O, and
N—$R^6$–$R^7$,
with the proviso that $R^5$ is not OH, alkoxy or N—$R^6$–$R^7$ when $R^4$ is C(=O)O—, that $R^5$ is not alkyl when $R^4$ is alkyl, alkenyl or alkynyl, and that $R^5$ is not a 6-membered fully saturated heterocycle having four carbon atoms and NH and O as heteroatoms when $R^4$ is CH$_2$;

$R^6$ and $R^7$ are independently selected from
hydrogen,
alkyl of 1–8 carbon atoms,
alkenyl of 2–8 carbon atoms, and
alkynyl of 2–8 carbon atoms,
or $R^6$ and $R^7$ combine together with the nitrogen atom to which they are attached to form a 5–7 membered, unsaturated ring which may contain 1–2 additional heteroatoms selected from N, S and O or to form a 5–7 membered, saturated ring which may contain 1–2 additional heteroatoms selected from NH, NR$^{11}$, S and O;

$R^8$ is selected from
alkyl of 4–8 carbon atoms,
alkenyl of 2–8 carbon atoms,
alkynyl of 2–8 carbon atoms,
$R^{12}$–$R^{13}$,
cycloalkyl of 3–7 carbon atoms,
fully saturated heterocycle of 2–6 carbon atoms and 1–2 heteroatoms selected from NH, S and O,
aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O,
heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O;

$R^9$ is selected from
alkyl of 1–8 carbon atoms,
alkenyl of 2–8 carbon atoms, and
alkynyl of 2–8 carbon atoms;

$R^{10}$ is selected from
OH,
aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O, and
heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O;

$R^{11}$ is selected from benzyl which may be substituted with
alkyl of 1–6 carbon atoms,
alkenyl of 2–6 carbon atoms,
alkynyl of 2–6 carbon atoms,
halogen, and
$R^{14}R^{15}$;

$R^{12}$ is selected from
alkyl of 1–8 carbon atoms,
alkenyl of 2–8 carbon atoms, and
alkynyl of 2–8 carbon atoms;

$R^{13}$ is selected from
cycloalkyl of 3–7 carbon atoms,
fully saturated heterocycle of 2–6 carbon atoms and 1–2 heteroatoms selected from NH, S and O,
aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O, and
heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O;

$R^{14}$ is alkyl of 1–3 carbon atoms;
$R^{15}$ is cycloalkyl of 3–7 carbon atoms;

with the proviso that when $R^3$ is hydrogen,
$R^1$ and $R^2$ are independently selected from
hydrogen, with the further proviso that only one of $R^1$ and $R^2$ may be hydrogen,
$CH_2$—$CH_2$—$N(CH_2CH_3)_2$,
$CH_2$—$CH_2SCH_3$,
bornyl, and

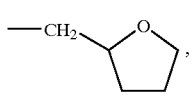, or $R^1$ and $R^2$ combine to form, together with the nitrogen atom to which they are attached, a six membered saturated ring which may contain 1–2 sulfur atoms, wherein said ring may be substituted with 1–2 substituents selected from the group consisting of alkyl of 2–8 carbon atoms, OH, $CH_2OH$;
or $R^1$ and $R^2$ combine to form, together with the nitrogen atom to which they are attached, a five membered saturated ring which also contains 1–2 sulfur atoms,
or $R^1$ and $R^2$ combine to form, together with the nitrogen atom to which they are attached, an 8–10 membered bicyclic saturated ring;

with the further proviso that when $R^3$ is methyl,
$R^1$ and $R^2$ are independently selected from the group consisting of
hydrogen,
alkyl of 1–8 carbon atoms,
alkenyl of 2–8 carbon atoms,
alkynyl of 2–8 carbon atoms,
cycloalkyl of 3–7 carbon atoms, and
bornyl;

with the further proviso that when $R^3$ is hydrogen or $C_2$–$C_4$ alkyl, then $R^1$ and $R^2$ may not combine to form a morpholino, piperidino, or piperazinyl group;

and pharmaceutically acceptable salts thereof.

11. The compound of claim 10, wherein $R^3$ is selected from the group consisting of:
alkyl of 2–8 carbon atoms,
alkenyl of 2–8 carbon atoms,
alkynyl of 2–8 carbon atoms,
cycloalkyl of 3–7 carbon atoms,
fully saturated heterocycle of 2–6 carbon atoms and 1–2 heteroatoms selected from NH, S and O,
aryl of 6–12 carbon atoms, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O,
heteroaryl of 4–11 carbon atoms and 1–2 heteroatoms selected from N, S and O, which may be substituted with alkyl of 1–6 carbon atoms, alkenyl of 2–6 carbon atoms, alkynyl of 2–6 carbon atoms, alkoxy of 1–6 carbon atoms, halogen, haloalkyl of 1–6 carbon atoms and a number of halogen atoms up to the perhalo level, haloalkoxy of 1–6 carbon atoms and a number of halogen atoms up to the perhalo level, aryl of 6–12 carbon atoms or heteroaryl of 4–11 carbon atoms and 1–2 heteroatoms selected from N, S and O, and $R^4$–$R^5$; and $R^4$ is selected from
alkyl of 2–8 carbon atoms,
alkenyl of 2–8 carbon atoms,
alkynyl 2–8 carbon atoms,
C(=O), and
S(=O)$_2$, with the proviso that when $R^3$ is $C_2$–$C_4$ alkyl, then $R^1$ and $R^2$ may not combine to form a morpholino, piperidino, or piperazinyl group.

12. A pharmaceutical composition comprising the compound of claim 10 and a pharmaceutically acceptable carrier.

* * * * *

UNITED STATES PATENT AND TRADEMARK OFFICE
CERTIFICATE OF CORRECTION

PATENT NO. : 6,849,638 B2
DATED : February 1, 2005
INVENTOR(S) : Andreas Stolle et al.

It is certified that error appears in the above-identified patent and that said Letters Patent is hereby corrected as shown below:

Column 83,
Line 48, "1-2heteroatoms" should read -- "1-2 heteroatoms" --.

Column 84,
Line 64, "$C(=O)_2$" should read -- "$C(=O)$" --.
Line 65, "$S(=O)$" should read -- "$S(=O)_2$" -- .

Column 88,
Line 13, "stunts" should read -- "atoms" --.

Column 91,
Line 8, "$N-R^6-R^1$" should read -- "$N-R^6-R^7$" --.

Column 92,
Line 18, "$R^{14-R15}$" should read -- "$R^{14}-R^{15}$" --.
Line 62, "$CH_3, CF_3$" should read -- "$CH_3$, or $CF_3$" --.

Column 93,
Line 2, "$R^3$" should read -- "$R^2$" --.

Column 94,
Line 43, "$R^1$ and combine" should read -- "$R^1$ and $R^2$ combine" --.

Column 97,
Line 8, "$R^{14}R^{15}$" should read -- "$R^{14}-R^{15}$" --.

Signed and Sealed this

Seventeenth Day of May, 2005

JON W. DUDAS
*Director of the United States Patent and Trademark Office*